US012691135B2

(12) United States Patent
Pandolfi et al.

(10) Patent No.: US 12,691,135 B2
(45) Date of Patent: Jul. 28, 2026

(54) INHIBITORS OF MICRO-RNA 22

(71) Applicants: Beth Israel Deaconess Medical Center, Boston, MA (US); Aalborg Univeristy, Aalborg (DK); Resalis Therapeutics srl, Turin (IT)

(72) Inventors: Pier Paolo Pandolfi, Boston, MA (US); Riccardo Panella, Boston, MA (US); Sakari Kauppinen, Aalborg (DK); Andreas Petri, Aalborg (DK)

(73) Assignees: Beth Israel Deaconess Medical Center, Boston, MA (US); Aalborg University, Aalborg (DK); Resalis Therapeutics srl, Turin (IT)

( * ) Notice: Subject to any disclaimer, the term of this patent is extended or adjusted under 35 U.S.C. 154(b) by 744 days.

(21) Appl. No.: 18/045,906

(22) Filed: Oct. 12, 2022

(65) Prior Publication Data

US 2023/0181613 A1 Jun. 15, 2023

Related U.S. Application Data

(63) Continuation-in-part of application No. 16/979,782, filed as application No. PCT/US2019/022351 on Mar. 14, 2019, now Pat. No. 11,499,152.

(60) Provisional application No. 62/642,934, filed on Mar. 14, 2018.

(51) Int. Cl.

| | |
|---|---|
| ***C07H 21/02*** | (2006.01) |
| ***A61K 31/712*** | (2006.01) |
| ***A61K 31/7125*** | (2006.01) |
| ***A61P 3/00*** | (2006.01) |
| ***C07H 21/04*** | (2006.01) |

(52) U.S. Cl.

CPC ........ *A61K 31/7125* (2013.01); *A61K 31/712* (2013.01); *A61P 3/00* (2018.01)

(58) Field of Classification Search

CPC ........................ C12N 15/113; C12N 2310/141

See application file for complete search history.

(56) References Cited

U.S. PATENT DOCUMENTS

| | | | | |
|---|---|---|---|---|
| 8,288,356 | B2 * | 10/2012 | Obad | C12N 15/111 514/44 A |
| 10,358,643 | B2 * | 7/2019 | Albaek | A61P 43/00 |
| 2007/0213292 | A1 * | 9/2007 | Stoffel | C12N 15/113 514/44 A |
| 2010/0004320 | A1 | 1/2010 | Elmen et al. | |
| 2012/0148664 | A1 | 6/2012 | Dalby et al. | |
| 2015/0111949 | A1 | 4/2015 | Pandolfi et al. | |

FOREIGN PATENT DOCUMENTS

| | | | | |
|---|---|---|---|---|
| AU | 2013254923 | A1 | 11/2013 | |
| WO | WO 2007/112754 | A2 | 10/2007 | |
| WO | WO 2013/181613 | A1 | 12/2013 | |
| WO | WO 2013/192576 | A1 | 12/2013 | |
| WO | WO 2016/127002 | A1 | 8/2016 | |
| WO | WO-2016149358 | A1 * | 9/2016 | A61K 31/194 |

OTHER PUBLICATIONS

Kim et al. (BioChip J, 2015, 9(1), 76-84).*
Yadav et al. (iLiver, 2, 2023, 1-9).*
Frieden et al. (Nucleic Acids Research, 2003, 31, 21, 6365-6372).*
Diniz et al. (Clin Sci (Lond). Dec. 15, 2017; 131(24): 2885-290).*
Lennox, et al., "Chemical modification and design of anti-miRNA oligonucleotides," Gene Therapy, vol. 18, No. 12, pp. 1111-1120, Jul. 14, 2011.
Gurha, "MicroRNAs in cardiovascular disease," Current Opinion in Cardiology, vol. 31, No. 3, pp. 249-254, May 3, 2016.
International Search Report & Written Opinion, PCT Application No. PCT/US19/22351, dated Jul. 29, 2019, 12 pages.

* cited by examiner

*Primary Examiner* — Amy Rose Hudson
(74) *Attorney, Agent, or Firm* — Morgan, Lewis & Bockius LLP

(57) ABSTRACT

The present disclosure provides compositions and methods that inhibit the activity of microRNAs, for example miR-22.

6 Claims, 28 Drawing Sheets

Specification includes a Sequence Listing.

FIG. 1

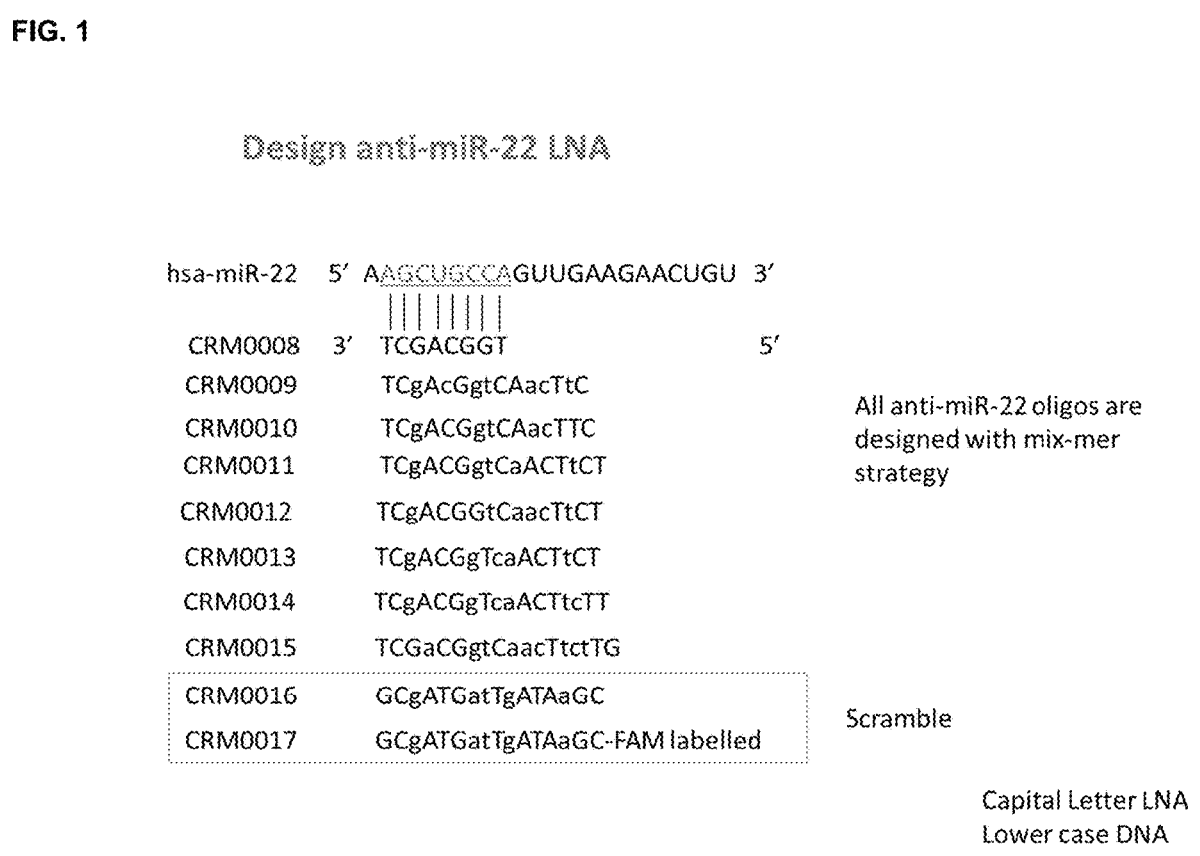

Design anti-miR-22 LNA

| | | |
|---|---|---|
| hsa-miR-22 | 5′ AAGCUGCCAGUUGAAGAACUGU 3′ | |
| CRM0008 | 3′ TCGACGGT 5′ | |
| CRM0009 | TCgAcGgtCAacTtC | All anti-miR-22 oligos are designed with mix-mer strategy |
| CRM0010 | TCgACGgtCAacTTC | |
| CRM0011 | TCgACGgtCaACTtCT | |
| CRM0012 | TCgACGGtCaacTtCT | |
| CRM0013 | TCgACGgTcaACTtCT | |
| CRM0014 | TCgACGgTcaACTtcTT | |
| CRM0015 | TCGaCGgtCaacTtctTG | |
| CRM0016 | GCgATGatTgATAaGC | Scramble |
| CRM0017 | GCgATGatTgATAaGC-FAM labelled | |

Capital Letter LNA
Lower case DNA

INHIBITORS OF MICRO-RNA 22

PRIORITY

This application is a U.S. Continuation-In-Part Application based on U.S. patent application Ser. No. 16/979,782 filed Sep. 10, 2020, which is a 35 U.S.C. § 371 national stage application of PCT/US2019/022351, filed on Mar. 14, 2019, and claims the benefit of, and claims priority to, U.S. Provisional Application No. 62/642,934, filed Mar. 14, 2018, the contents of which are incorporated herein by reference in their entireties.

FIELD OF THE DISCLOSURE

The disclosure relates to the agents that modulate the activity or expression of microRNAs.

DESCRIPTION OF THE TEXT FILE SUBMITTED ELECTRONICALLY

The instant application contains a sequence listing, which has been submitted in XML format via EFS-Web. The contents of the XML copy named "BID-005US2CP1_110304-5005 Sequence Listing", which was created on Oct. 10, 2022 and is 29,000 bytes in size, the contents of which are incorporated herein by reference in their entirety.

BACKGROUND

MicroRNAs (miRNAs) function as important post-transcriptional regulators of gene expression in many developmental and cellular processes, and have been implicated in the pathogenesis and progression of a wide range of human diseases. MiRNAs have become a new class of targets for therapeutic intervention and, thus, there is a need for compositions and methods that modulate miRNA activity.

SUMMARY

The present disclosure provides new compositions and methods for inhibiting miR-22, for example by inhibiting microRNA expression and/or activity. Such inhibition can be mediated by chemically modified anti-sense oligonucleotides, complementary to the cognate mature microRNA sequence, including for example, locked nucleic acid (LNA) modified antisense oligonucleotides.

In one aspect, the present invention provides a miR-22 inhibitory composition. The composition comprises a nucleic acid having a sequence comprising tggcagct (SEQ ID NO: 2) and comprising at least one locked nucleic acid (LNA) modification.

In embodiments, the nucleic acid comprises LNA modifications at positions 7 and 8 of tggcagct (SEQ ID NO: 2). In embodiments, the nucleic acid comprises about 8 to about 12 LNA modifications. In embodiments, the nucleic acid comprises no less than 4 LNA modifications. In embodiments, the nucleic acid comprises no more than four sequential LNA modifications.

In embodiments, the nucleic acid comprises a nucleic acid having a sequence selected from: tggcagct (SEQ ID NO: 2), cttcaactggcagct (SEQ ID NO: 3), tcttcaactggcagct (SEQ ID NO: 4), ttcttcaactggcagct (SEQ ID NO: 5), and gttcttcaactggcagct (SEQ ID NO: 6). In embodiments, the nucleic acid comprises about 8 to about 12 LNA modifications, e.g., about 8 to about 10 LNA modifications. In embodiments, the nucleic acid comprises about 8, or about 9, or about 10, or about 11, or about 12 LNA modifications.

In embodiments, the nucleic acid comprises tggcagct (SEQ ID NO: 2), and at least 6 LNA modifications.

In embodiments, the nucleic acid comprises tggcagct (SEQ ID NO: 2), and at least 8 LNA modifications.

In embodiments, the nucleic acid comprises cttcaactggcagct (SEQ ID NO: 3), and at least 6 LNA modifications, at least 8 LNA modifications, or at least 10 LNA modifications. In embodiments, the nucleic acid comprises cttcaactggcagct (SEQ ID NO: 3), and 8 LNA modifications, said modifications being at positions 1, 3, 6, 7, 10, 12, 14, and 15. In embodiments, the nucleic acid comprises cttcaactggcagct (SEQ ID NO: 3), and 10 LNA modifications, said modifications being at positions 1, 2, 3, 6, 7, 10, 11, 12, 14, and 15.

In embodiments, the nucleic acid comprises tcttcaactggcagct (SEQ ID NO: 4), and at least 8 LNA modifications, at least 10 LNA modifications, or at least 11 LNA modifications. In embodiments, the nucleic acid comprises tcttcaactggcagct (SEQ ID NO: 4), and 10 LNA modifications, said modifications being at positions 1, 2, 4, 8, 10, 11, 12, 13, 15, and 16. In embodiments, the nucleic acid comprises tcttcaactggcagct (SEQ ID NO: 4), and 11 LNA modifications, said modifications being at positions 1, 2, 4, 5, 6, 8, 11, 12, 13, 15, and 16. In embodiments, the nucleic acid comprises tcttcaactggcagct (SEQ ID NO: 4), and 11 LNA modifications, said modifications being at positions 1, 2, 4, 5, 6, 9, 11, 12, 13, 15, and 16.

In embodiments, the nucleic acid comprises ttcttcaactggcagct (SEQ ID NO: 5), and at least 10 LNA modifications or at least 11 LNA modifications. In embodiments, the nucleic acid comprises ttcttcaactggcagct (SEQ ID NO: 5), and 11 LNA modifications, said modifications being at positions 1, 2, 5, 6, 7, 10, 12, 13, 14, 16, and 17.

In embodiments, the nucleic acid comprises gttcttcaactggcagct (SEQ ID NO: 6), and at least 9 LNA modifications or at least 10 LNA modifications. In embodiments, the nucleic acid comprises gttcttcaactggcagct (SEQ ID NO: 6), and 9 LNA modifications, said modifications being at positions 1, 2, 6, 10, 13, 14, 16, 17, and 18.

In embodiments, the nucleic acids comprise about 17 to about 20 nucleotides in length (e.g., about 17, or 18, or 19, or 20, residues in length). In embodiments, the nucleic acids are about 17 nucleotides in length. In embodiments, the nucleic acids are about 18 nucleotides in length. In embodiments, the nucleic acids are about 19 nucleotides in length. In embodiments, the nucleic acids are about 20 nucleotides in length.

In another aspect, the present invention provides a pharmaceutical composition comprising the nucleic acid of the above aspect or any of the above embodiments and a pharmaceutically acceptable excipient or carrier.

In yet another aspect, the present invention provides a vector or a plasmid comprising a nucleic acid of the above aspect or any of the above embodiments.

An aspect of the present invention provides a host cell comprising a nucleic acid of the above aspect or any of the above embodiments.

Another aspect of the present invention provides a method for inhibiting miR-22. The method comprising contacting miR-22 with a composition comprising an inhibitor of miR-22 that is a nucleic acid of the above aspect or any of the above embodiments.

In another aspect, the present invention provides a miR-22 inhibitory composition comprising a nucleic acid having a sequence consisting of gttcttcaactggcagct (SEQ ID NO: 6), wherein the nucleic acid comprises at least 6, or at least 8 locked nucleic acid (LNA) modifications.

In some embodiments, the nucleic acid sequence comprises at least 10, or at least 11, or at least 12 locked nucleic acid (LNA) modifications.

In some embodiments, the nucleic acid comprises at least 10, or at least 11, locked nucleic acid (LNA) modifications.

In some embodiments, the nucleic acid comprises 10 or 11 LNA modifications, said modifications being at least at positions 1, 2, 6, 11, 17, 18.

In some embodiments, the nucleic acid comprises 11 LNA modifications, said modifications being at least at positions 1, 2, 5, 6, 11, 14, 17, 18.

In some embodiments, the nucleic acid sequence comprises at least one internucleotide linkage, wherein the internucleotide linkage is a PS (Phosphorothioate) linkage substituted with one PO (Phosphine Oxide) linkage.

In some embodiments, one PS linkage is substituted with one PO linkage.

In some embodiments, the PO linkage is at least at positions 6, 8, 10, or 14.

In some embodiments, the PO linkage is only one, and the PO linkage is at position 6, 10, or 14.

In some embodiments, the nucleic acid comprises a nucleic acid having a sequence selected from the group consisting of: GTtcTTCaAcTGgCagCT (SEQ ID NO: 17), GTtCtTcAaCTggcAgCT (SEQ ID NO: 19), or GTtcTTcAaCtgGCAgCT (SEQ ID NO: 20), where the capital letters are LNA modifications, and the lower case letters are unmodified.

In some embodiments, the nucleic acid comprises a nucleic acid having a sequence selected from the group consisting of: G*T*t*c*T*TC*a*A*c*T*G*g*C*a*g*C*T (SEQ ID NO: 17), G*T*t*C*t*T*c*A*a*CT*g*g*c*A*g*C*T (SEQ ID NO: 19), G*T*t*c*T*T*c*A*a*C*t*g*G*CA*g*C*T (SEQ ID NO: 20), where the capital letters are LNA modifications, the lower case are unmodified, the symbol * denotes PS linkages, and the absence of the * symbol is denotes PO linkages.

In another aspect, the present invention provides a pharmaceutical composition comprising the nucleic acid of any one of the preceding embodiments, and a pharmaceutically acceptable excipient or carrier.

In another aspect, the present invention provides a vector or plasmid comprising the nucleic acid of any one of the preceding embodiments.

In another aspect, the present invention provides a host cell comprising the nucleic acid of any one of the preceding embodiments.

In another aspect, the present invention provides a method for inhibiting miR-22 comprising contacting miR-22 with a miR-22 inhibitory composition of any one of the preceding embodiments. In some embodiments, the present invention provides a method of treating a metabolic disorder in a subject, the method comprising administrating the pharmaceutical composition to the subject.

Any aspect or embodiment described herein can be combined with any other aspect or embodiment as disclosed herein.

BRIEF DESCRIPTION OF THE DRAWINGS

FIG. 1 shows the design of anti-miR-22 LNA. SEQ ID NO: 1, SEQ ID NO: 2, and SEQ ID NO: 7 to SEQ ID NO: 15 are shown.

FIGS. 6A and 6B are western blot images showing TET2 expression relative to HSP-90 control. FIG. 6C is a bar graph showing TET2 protein expression. In FIG. 6C, the order of data in the bar graphs, reading from left to right, is SCR (in black), 25 nM (in light grey), and 100 nM (in dark grey).

FIG. 10A shows the final percentage of body weight increase. FIG. 10B shows results from pharmacologic inhibition of miR-22 in DIO mice. In both figures (FIG. 10A and FIG. 10B), at the final time points, the order of data going from top to bottom is Vehicle (circles, first line appearing at about the 100% value on the y-axis), SCR (triangles, second line appearing under the vehicle line), and anti-miR-22 (squares, third line appearing under the SCR line).

DETAILED DESCRIPTION OF THE DISCLOSURE

Figure 2A:
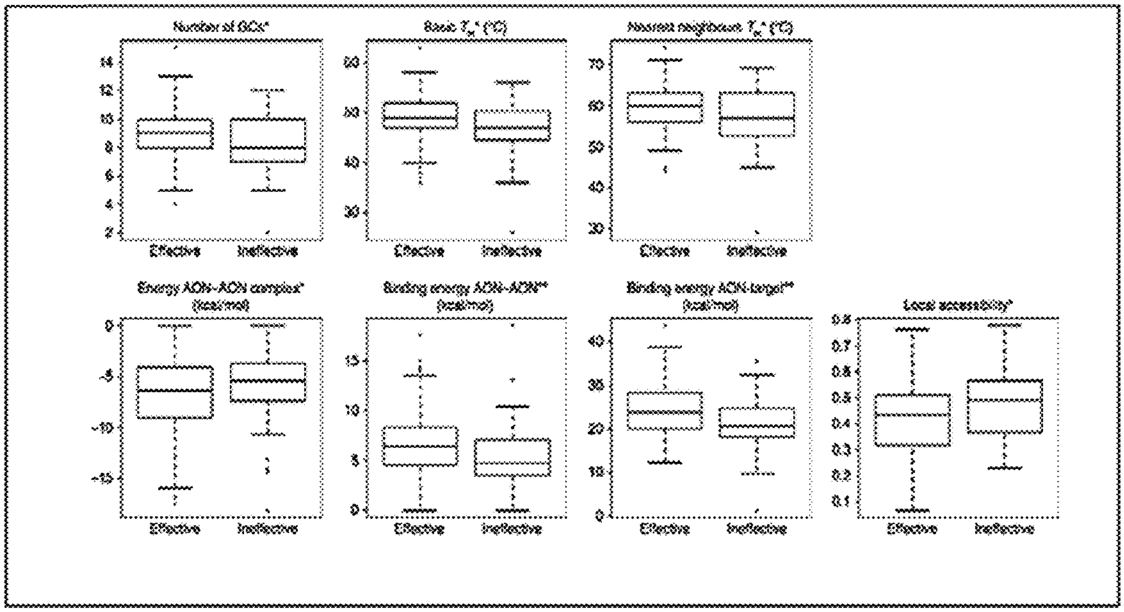
FIG. 2A, FIG. 2B, and FIG. 2C are a series of bar graphs and a line graphs that show the design space for anti-miR-22 oligonucleotides.
Figure 2B:
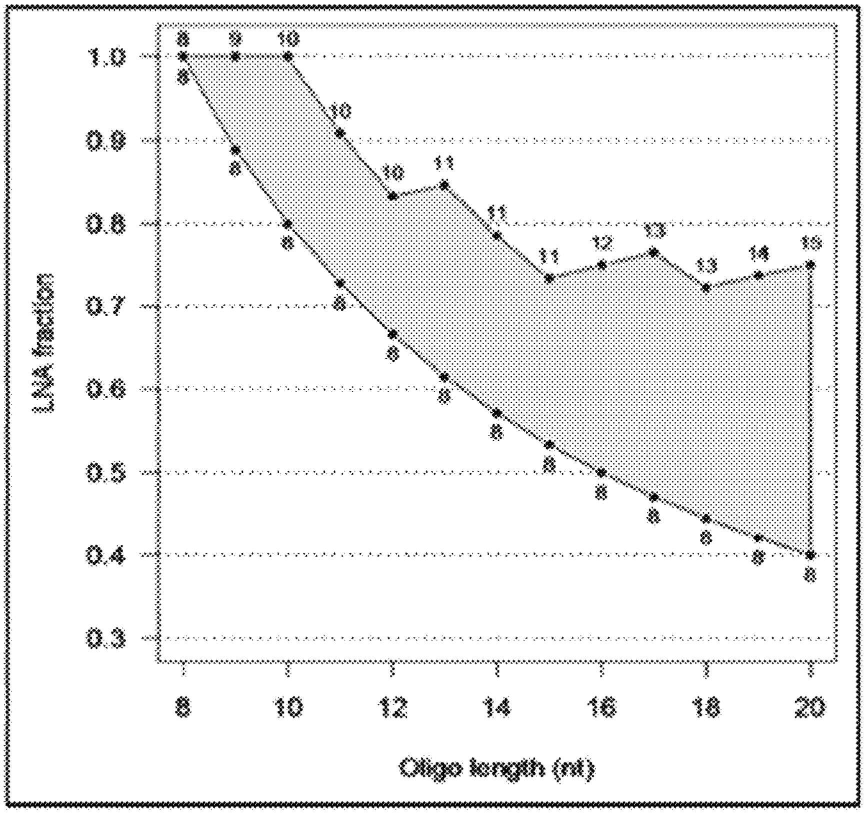
Figure 2C:
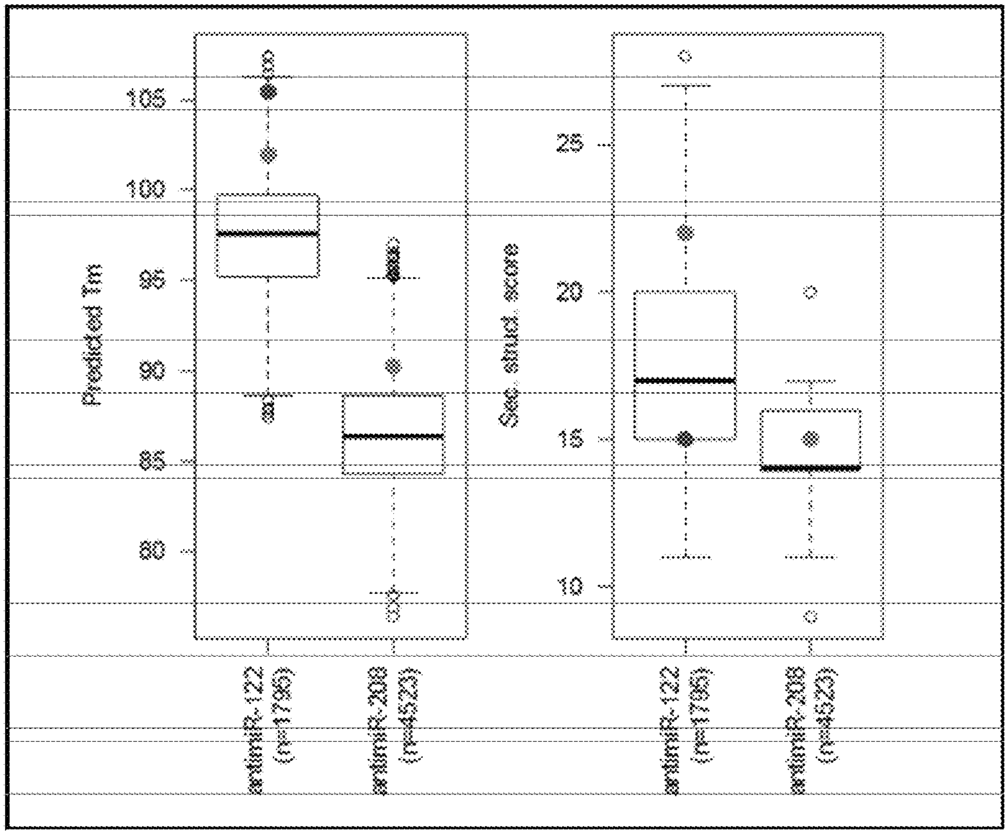

The present disclosure provides new compositions and methods for inhibiting miR-22, for example by inhibiting microRNA expression and/or activity.

Without being bound by theory, mature miRNAs are believed to be generated by pol II or pol III and arise from initial transcripts termed pri-miRNAs. These pri-miRNAs are frequently several thousand bases long and are therefore processed to make much shorter mature miRNAs. These pri-miRNAs may be multicistronic and result from the transcription of several clustered sequences that organize what may develop into many miRNAs. The processing to yield miRNAs may be two-steps. First, pri-miRNAs may be processed in the nucleus by the RNase Drosha into about 70- to about 100-nucleotide hairpin-shaped precursors (pre-miRNAs). Second, after transposition to the cytoplasm, the hairpin pre-miRNAs may be further processed by the RNase Dicer to produce a double-stranded miRNA. The mature miRNA strand may then be incorporated into the RNA-induced silencing complex (RISC), where it may associate with its target mRNAs by base-pair complementarity and lead to suppression of protein expression. The other strand of the miRNA duplex that is not preferentially selected for entry into a RISC silencing complex is known as the passenger strand or minor miRNA or star (*) strand. This strand may be degraded. It is understood that, unless specified, as used herein a miRNA may refer to pri- and/or pre- and/or mature and/or minor (star) strand and/or duplex version of miRNA.

In some embodiments, miRNA genes may be located within introns of protein-coding genes or within introns or exons of noncoding transcriptional units. The expression of intronic miRNAs may coincide with that of the hosting transcriptional units because they are typically oriented in the same direction and are coordinately expressed with the pre-mRNAs in which they reside.

In some embodiments, miRNAs may bind to sequences within the 3' untranslated region (3'UTR) of target gene transcripts. In some embodiments, miRNAs may bind to sequences outside of the 3'UTR of target gene transcripts. In some embodiments, miRNAs may bind to both within and outside the 3'UTR of target gene transcripts.

In some embodiments, nucleotide pairing between the second and seventh nucleotides of the miRNA (the miRNA seed sequence) and the corresponding sequence along the target 3'UTR (seed match) may occur for target recognition. Accordingly, the binding between miRNA and target may comprise about a 5 nucleotide base pairing. Additionally, the binding between miRNA and target may comprise more than a 5 nucleotide base pairing. In some embodiments, the binding between an miRNA and the gene that it regulates may be mediated by the miRNA binding up to 2, up to 4, up to 6, up to 8, or up to 10 sites of the target nucleic acid.

MicroRNA-22 (miR-22)

MiR-22 is highly conserved across many vertebrate species, including chimp, mouse, rat, dog and horse. This level of conservation suggests functional importance. MiR-22 was previously identified as having a role in erythrocyte maturation and later as having a role in oncogenesis. MiR-22 directly targets phosphatase and tensin homolog (PTEN) and tet methylcytosine dioxygenase (TET) to promote tumorigenesis, metastasis and metabolic disorders. In some embodiments, the nucleic acids of the present invention increase the activity and/or expression of PTEN and/or TET2.

The predicted miR-22 hairpin precursor is contained entirely within exon 2 of a noncoding transcript, C17orf91, and the splicing pattern is generally conserved in human and mouse, despite the lack of protein-coding potential. See Rodriguez et al., Identification of mammalian microRNA host genes and transcription units. Genome Res. 2004 October; 14(10A):1902-10. Deletion of exon 2 of C17orf91 encompassing mir-22 in mouse models has revealed that miR-22 may play a role in cardiac hypertrophy and remodeling by targeting SIRT1 (NAD-dependent deacetylase sirtuin-1), HDAC4 (histone deacetylase 4), PURB (purine-rich element binding protein B) and PTEN. See Gurha et al., Targeted deletion of microRNA-22 promotes stress-induced cardiac dilation and contractile dysfunction. Circulation. 2012 Jun. 5; 125(22):2751-61; Huang et al., MicroRNA-22 regulates cardiac hypertrophy and remodeling in response to stress. Circ Res. 2013 Apr. 26; 112(9):1234-43.

Inhibitors of miR-22

In embodiments, an inhibitor of miRNA is a nucleic acid that acts as an antisense oligonucleotide. Nucleic acids of the present invention can include ribonucleotides or deoxyribonucleotides or a combination thereof. Nucleic acids of the present invention may have at least one chemical modification (non-limiting examples are sugar or backbone modifications, e.g., a Locked Nucleic Acid (LNA)).

In embodiments, the sequence of a nucleic acid that inhibits miR-22 is conserved across species. In embodiments, the sequence of the nucleic acid is complementary, in part, to the sequence of human miR-22. In embodiments, the inhibitor is selected to reduce the expression and/or activity of the target miR-22 in a cell or a subject.

In embodiments, nucleic acids of the present invention inhibit human miR-22. In embodiments, human miR-22 comprises or consists of AAGCUGCCAGUUGAAGAACUGU (SEQ ID NO: 1).

In embodiments, the nucleic acids of the present invention are about 8 to about 20 residues in length (e.g., about 8-18, or about 8-16, or about 8-14, or about 8-12, or about 8-10, or about 10-18, or about 10-16, or about 10-14, or about 10-12 residues in length). In embodiments, the nucleic acids are about 8, or about 9, or about 10, or about 11, or about 12 residues in length.

In embodiments, nucleic acids of the present invention bind with complete homology to a portion of miR-22. For example, a nucleic acid of the present invention may be 18 residues in length and each of the 18 residues is complementary to a nucleotide of miR-22. Alternately, the nucleic acids of the present invention bind with complete homology to a portion of miR-22. For example, for a nucleic acid of the present invention may be 16 residues in length and only 15 or fewer of the residues are complementary to a nucleotide of miR-22.

In embodiments, a nucleic acid of the present invention differs from a portion of miR-22 at one position, at two positions, at three positions, at four positions, at five positions, or at more than five positions.

In embodiments, a nucleic acid of the present invention binds to miR-22 with sufficient affinity to inhibit it. In embodiments, the nucleic acids bind to miR-22 with a high affinity (e.g. nM affinity). Thus, a nucleic acid of the present invention binds to miR-22 with a high affinity even if it differs from a portion of miR-22 at one or more positions.

A nucleic acid of the present invention may have a sequence comprising tggcagct (SEQ ID NO: 2) and comprising at least one locked nucleic acid (LNA) modification.

In a locked nucleic acid (LNA) the nucleic acid's ribose moiety is modified with an extra bridge connecting the 2' oxygen and 4' carbon, which locks the ribose in the 3'-endo conformation.

Nucleic acids of the present invention, and comprising LNAs, provide for cost-effective agents that can be delivered efficiently and possess sufficient bioavailability for the treatment and prevention of various disorders.

In embodiments, a nucleic acid of the present invention includes at least 2 LNA modifications towards its 3' end (e.g., about 2, or about 3, or about 4, or about 5 modifications towards its 3' end). In embodiments, the nucleic acid comprises tggcagct (SEQ ID NO: 2), and at least 6 LNA modifications or at least 8 LNA modifications.

For example, the nucleic acid comprises LNA modifications at positions 7 and 8 of tggcagct (SEQ ID NO: 2). In embodiments, a nucleic acid of the present invention includes no more than 4 sequential LNA modifications (e.g., only 2, or 3, or 4 sequential LNA modifications). In embodiments, a nucleic acid of the present invention includes no more than 3 sequential unmodified residues (e.g., only 3, or 2, or 1 unmodified residues). In embodiments, a nucleic acid of the present invention includes no less than 4 LNA modifications. In embodiments, the nucleic acid comprises about 8 to about 12 LNA modifications, e.g., about 8, or about 9, or about 10, or about 11, or about 12 LNA modifications.

In embodiments, the nucleic acid comprises or consists of a nucleic acid having a sequence selected from: tggcagct (SEQ ID NO: 2), cttcaactggcagct (SEQ ID NO: 3), tcttcaactggcagct (SEQ ID NO: 4), ttcttcaactggcagct (SEQ ID NO: 5), and gttcttcaactggcagct (SEQ ID NO: 6). In embodiments, the nucleic acid comprises a nucleic acid having a sequence selected from: tggcagct (SEQ ID NO: 2), cttcaactggcagct (SEQ ID NO: 3), tcttcaactggcagct (SEQ ID NO: 4), ttcttcaactggcagct (SEQ ID NO: 5), and gttcttcaactggcagct (SEQ ID NO: 6) and comprising about 8 to about 12 LNA modifications, e.g., about 8, or about 9, or about 10, or about 11, or about 12 LNA modifications.

In embodiments, the nucleic acid comprises or consists of cttcaactggcagct (SEQ ID NO: 3), and at least 6 LNA modifications, at least 8 LNA modifications, or at least 10 LNA modifications. In embodiments, the nucleic acid comprises or consists of cttcaactggcagct (SEQ ID NO: 3), and 8 LNA modifications, said modifications being at positions 1, 3, 6, 7, 10, 12, 14, and 15; for example, the nucleic acid comprises or consists of the sequence CtTcaACtgGcAgCT (SEQ ID NO: 7), where capital letters are LNA modified and lower case are unmodified. In embodiments, the nucleic acid comprises or consists cttcaactggcagct (SEQ ID NO: 3), and 10 LNA modifications, said modifications being at positions 1, 2, 3, 6, 7, 10, 11, 12, 14, and 15; for example, the nucleic acid comprises or consists of the sequence CTTcaACtgGCAgCT (SEQ ID NO: 8), where capital letters are LNA modified and lower case are unmodified.

In embodiments, the nucleic acid comprises or consists of tcttcaactggcagct (SEQ ID NO: 4), and at least 8 LNA modifications, at least 10 LNA modifications, or at least 11 LNA modifications. In embodiments, the nucleic acid comprises or consists of tcttcaactggcagct (SEQ ID NO: 4), and 10 LNA modifications, said modifications being at positions 1, 2, 4, 8, 10, 11, 12, 13, 15, and 16; for example, the nucleic acid comprises or consists of the sequence TCtTcaaCtGGCAgCT (SEQ ID NO: 10), where capital letters are LNA modified and lower case are unmodified. In embodiments, the nucleic acid comprises or consists of tcttcaactggcagct (SEQ ID NO: 4), and 11 LNA modifications, said modifications being at positions 1, 2, 4, 5, 6, 8, 11, 12, 13, 15, and 16; for example, the nucleic acid comprises or consists of the sequence TCtTCAaCtgGCAgCT (SEQ ID NO: 9), where capital letters are LNA modified and lower case are unmodified.

In embodiments, the nucleic acid comprises or consists of tcttcaactggcagct (SEQ ID NO: 4), and 11 LNA modifications, said modifications being at positions 1, 2, 4, 5, 6, 9, 11, 12, 13, 15, and 16; for example, the nucleic acid comprises or consists of the sequence TCtTCAacTgGCAgCT (SEQ ID NO: 11), where capital letters are LNA modified and lower case are unmodified.

In embodiments, the nucleic acid comprises or consists of ttcttcaactggcagct (SEQ ID NO: 5), and at least 10 LNA modifications or at least 11 LNA modifications. In embodiments, the nucleic acid comprises or consists of ttcttcaactggcagct (SEQ ID NO: 5), and 11 LNA modifications, said modifications being at positions 1, 2, 5, 6, 7, 10, 12, 13, 14, 16, and 17; for example, the nucleic acid comprises or consists of the sequence TTctTCAacTgGCAgCT (SEQ ID NO: 12), where capital letters are LNA modified and lower case are unmodified.

In embodiments, the nucleic acid comprises or consists of gttcttcaactggcagct (SEQ ID NO: 6), and at least 9 LNA modifications or at least 10 LNA modifications. In embodiments, the nucleic acid comprises or consists of gttcttcaactggcagct (SEQ ID NO: 6), and 9 LNA modifications, said modifications being at positions 1, 2, 6, 10, 13, 14, 16, 17, and 18; for example, the nucleic acid comprises or consists of the sequence GTtctTcaaCtgGCaGCT (SEQ ID NO: 13), where capital letters are LNA modified and lower case are unmodified.

In embodiments, the nucleic acid comprises or consists of a nucleic acid having a sequence selected from: tggcagct (SEQ ID NO: 2), gttcttcaactggcagct (SEQ ID NO: 6), and comprising about 8 to about 12 LNA modifications, e.g., about 8, or about 9, or about 10, or about 11, or about 12 LNA modifications.

In embodiments, the nucleic acid comprises or consists of gttcttcaactggcagct (SEQ ID NO: 6), and at least 9 LNA modifications, or at least 10 LNA modifications, or at least 11 LNA modifications, or at least 12 LNA modifications.

In an embodiment, the nucleic acid comprises at least 10, or at least 11, or at least 12 locked nucleic acid (LNA) modifications.

In an embodiment, the nucleic acid comprises 10 or 11 locked nucleic acid (LNA) modifications.

In an embodiment, the nucleic acid consists of gttcttcaactggcagct (SEQ ID NO: 6), and comprises 10 or 11 modifications, said modifications being at least at positions 1, 2, 6, 11, 17, 18.

In an embodiment, the nucleic acid consists of gttcttcaactggcagct (SEQ ID NO: 6), and comprises 11 modifications, said modifications being at least at positions 1, 2, 5, 6, 11, 14, 17, 18.

In an embodiment, the nucleic acid consists of gttcttcaactggcagct (SEQ ID NO: 6), and at least one PS (Phosphorothioate) linkage has been substituted with one PO (Phosphine Oxide) linkage.

In an embodiment, the nucleic acid consists of gttcttcaactggcagct (SEQ ID NO: 6) and one PS linkage has been substituted with one PO linkage.

In an embodiment said PO linkage is at least at positions 6, 8, 10, or 14.

In an embodiment, said PO linkage is only one and it is at position 6, 10, or 14.

For example, the nucleic acid comprises or consists of the sequence GTTctTcAAcTGgCAgCT (SEQ ID NO: 16), where capital letters are LNA modified and lower case are unmodified.

For example, the nucleic acid comprises or consists of the sequence GTtcTTCaAcTGgCagCT (SEQ ID NO: 17), where capital letters are LNA modified and lower case are unmodified.

For example, the nucleic acid comprises or consists of the sequence GTtcTTcAaCTGgCAgCT (SEQ ID NO: 18), where capital letters are LNA modified and lower case are unmodified.

For example, the nucleic acid comprises or consists of the sequence GTtCtTcAaCTggcAgCT (SEQ ID NO: 19), where capital letters are LNA modified and lower case are unmodified.

For example, the nucleic acid comprises or consists of the sequence GTtcTTcAaCtgGCAgCT (SEQ ID NO: 20), where capital letters are LNA modified and lower case are unmodified.

The present invention provides a method for inhibiting miR-22. The method comprising contacting miR-22 with a composition comprising an inhibitor of miR-22 that is a nucleic acid of the aspects or embodiments described herein.

In another aspect, the present invention provides a miR-22 inhibitory composition comprising a nucleic acid having a sequence consisting of gttcttcaactggcagct (SEQ ID NO: 6), wherein the nucleic acid comprises at least 6, or at least 8 locked nucleic acid (LNA) modifications.

In some embodiments, the nucleic acid sequence comprises at least 10, or at least 11, or at least 12 locked nucleic acid (LNA) modifications.

In some embodiments, the nucleic acid comprises at least 10, or at least 11, locked nucleic acid (LNA) modifications.

In some embodiments, the nucleic acid comprises 10 or 11 LNA modifications, said modifications being at least at positions 1, 2, 6, 11, 17, 18.

In some embodiments, the nucleic acid comprises 11 LNA modifications, said modifications being at least at positions 1, 2, 5, 6, 11, 14, 17, 18.

In some embodiments, the nucleic acid sequence comprises at least one internucleotide linkage, wherein the internucleotide linkage is a PS (Phosphorothioate) linkage substituted with one PO (Phosphine Oxide) linkage.

In some embodiments, one PS linkage is substituted with one PO linkage.

In some embodiments, the PO linkage is at least at positions 6, 8, 10, or 14.

In some embodiments, the PO linkage is only one, and the PO linkage is at position 6, 10, or 14.

In some embodiments, the nucleic acid comprises a nucleic acid having a sequence selected from the group consisting of: GTtcTTCaAcTGgCagCT (SEQ ID NO: 17), GTtCtTcAaCTggcAgCT (SEQ ID NO: 19), or GTtcTTcAaCtgGCAgCT (SEQ ID NO: 20), where the capital letters are LNA modifications, and the lower case letters are unmodified.

In some embodiments, the nucleic acid comprises a nucleic acid having a sequence selected from the group consisting of: G*T*t*c*T*TC*a*A*c*T*G*g*C*a*g*C*T (SEQ ID NO: 17), G*T*t*C*t*T*c*A*a*CT*g*g*c*A*g*C*T (SEQ ID NO: 19), G*T*t*c*T*T*c*A*a*C*t*g*G*CA*g*C*T (SEQ ID NO: 20), where the capital letters are LNA modifications, the lower case are unmodified, the symbol * denotes PS linkages, and the absence of the * symbol denotes PO linkages.

In another aspect, the present invention provides a pharmaceutical composition comprising the nucleic acid of any one of the aspects or embodiments provided herein, and a pharmaceutically acceptable excipient or carrier.

In another aspect, the present invention provides a vector or plasmid comprising the nucleic acid of any of the embodiments provided herein.

In another aspect, the present invention provides a host cell comprising the nucleic acid of any one of any of the embodiments provided herein.

In another aspect, the present invention provides a method for inhibiting miR-22 comprising contacting miR-22 with a miR-22 inhibitory composition of any one of the preceding embodiments. In some embodiments, the present invention provides a method of treating a metabolic disorder in a subject, the method comprising administrating the pharmaceutical composition to the subject.

In embodiments, the nucleic acid comprising a sequence listed above, may further include additional nucleotides 5' to a herein-listed sequence and/or include additional nucleotides 3' to a herein-listed sequence. The additional nucleotides may be unmodified or may be modified, e.g., LNA or an additional chemical modification.

In some embodiments, a nucleic acid of the present invention may further include additional chemical modification. As examples, the chemical modification is one or more of a phosphorothioate, 2'-0-Methyl, or 2'-O-Methoxyethyl, 2'-0-alkyl-RNA unit, 2'-OMe-RNA unit, 2'-amino-DNA unit, 2'-fluoro-DNA unit (including, but not limited to, a DNA analogue with a substitution to a fluorine at the 2' position (2' F)), LNA unit, PNA unit, HNA unit, INA unit, and a 2' MOE RNA unit.

Suitable nucleic acids can be comprised of one or more conformationally constrained or bicyclic sugar nucleoside modifications (BSN) that confer enhanced thermal stability to complexes formed between the oligonucleotide containing BSN and their complementary miRNA target strand. For example, in one embodiment, the nucleic acids contain at least one locked nucleic acid. Locked nucleic acids (LNAs) contain a 2'-0, 4'-C-methylene ribonucleoside (structure A) wherein the ribose sugar moiety is in a locked conformation. In another embodiment, the nucleic acids contain at least one 2', 4'-C-bridged 2' deoxyribonucleoside (CDNA, structure B). See, e.g., U.S. Pat. No. 6,403,566 and Wang et al., (1999) Bioorganic and Medicinal Chemistry Letters, Vol. 9: 1147-1150, both of which are herein incorporated by reference in their entireties. In yet another embodiment, the nucleic acids contain at least one modified nucleoside having the structure shown in structure C. The nucleic acids targeting miRNAs that regulate fat related metabolism and synthesis pathway targets can contain combinations of BSN (LNA, CDNA, and the like) or other modified nucleotides, and ribonucleotides or deoxyribonucleotides.

A.

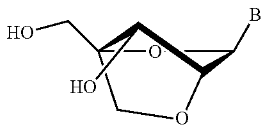

-continued

B.

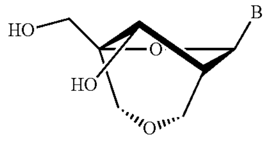

C.

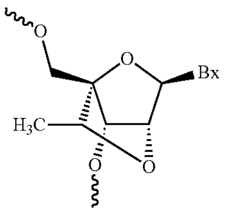

Alternatively, the nucleic acids can comprise peptide nucleic acids (PNAs), which contain a peptide-based backbone rather than a sugar-phosphate backbone. Other modified sugar or phosphodiester modifications to the nucleic acids are also contemplated. By way of non-limiting examples, other chemical modifications can include 2'-o-alkyl (e.g., 2'-0-methyl, 2'-o-methoxyethyl), 2'-fluoro, and 4'-thio modifications, and backbone modifications, such as one or more phosphorothioate, morpholino, or phosphonocarboxylate linkages (see, e.g., U.S. Pat. Nos. 6,693,187 and 7,067,641, which are herein incorporated by reference in their entireties). In one embodiment, nucleic acids targeting oncogenic miRNAs contain 2'-0-methyl sugar modifications on each base and are linked by phosphorothioate linkages. Nucleic acids, particularly those of shorter lengths (e.g., less than 16 nucleotides, 7-8 nucleotides) can comprise one or more affinity enhancing modifications, such as, but not limited to, LNAs, bicyclic nucleosides, phosphonoformates, 2' o-alkyl modifications, and the like. In some embodiments, suitable nucleic acids are 2'-0-methoxyethyl gapmers which contain 2'-O-methoxyethyl-modified ribonucleotides on both 5' and 3' ends with at least ten deoxyribonucleotides in the center. These gapmers are capable of triggering RNase H-dependent degradation mechanisms of RNA targets. Other modifications of nucleic acids to enhance stability and improve efficacy, such as those described in U.S. Pat. No. 6,838,283, which is herein incorporated by reference in its entirety, are known in the art and are suitable for use in the methods of the invention. For instance, and not intending to be limiting, to facilitate in vivo delivery and stability, the nucleic acids can be linked to a steroid, such as cholesterol moiety, a vitamin, a fatty acid, a carbohydrate or glycoside, a peptide, or other small molecule ligand at its 3' end.

As used herein, substantially complementary refers to a sequence that is at least about 95%, 96%, 97%, 98%, 99%, or 100% complementary to a target polynucleotide sequence (non-limiting examples are mature, minor, precursor miRNA, or pri-miRNA sequence of, for example, miR-22).

In some embodiments, the nucleic acid of the present invention is an antagomir. Antagomirs are single-stranded, chemically-modified ribonucleotides that are at least partially complementary to miRNAs and therefore may silence them. See, e.g., Kriitzfeldt, et al., Nature (2005) 438 (7068): 685-9. Antagomirs may comprise one or more modified nucleotides, such as 2'-0-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting can be about 15 to about 50 nucleotides in length, about 18 to about 30 nucleotides in length, and about 20 to about 25 nucleotides in length. The antagomirs can be at least about 75%, 80%, 85%, 90%, 95%, 96%, 97%, 98%, or 99% complementary to a mature or minor oncogenic miRNA sequence. In some embodiments, the antagomir may be substantially complementary to a mature or minor oncogenic miRNA sequence, that is at least about 95%, 96%, 97%, 98%, or 99% complementary to a target polynucleotide sequence. In other embodiments, the antagomirs are 100% complementary to a mature or minor oncogenic miRNA sequence.

Nucleic acids of the present invention may comprise a sequence that is substantially complementary to a precursor miRNA sequence (pre-miRNA) or primary miRNA sequence (pri-miRNA) of an oncogenic miRNA. In some embodiments, nucleic acids of the present invention comprises a sequence that is located outside the 3'-untranslated region of a target of that miRNA. In some embodiments, nucleic acids of the present invention comprises a sequence that is located inside the 3'-untranslated region of a target of that miRNA.

In embodiments, the nucleic acids have limited or no self-binding affinity. In embodiments, the nucleic acids have limited or no duplex structures. In embodiments, the nucleic acids have limited or no fold structures.

Any nucleic acids of the present invention can be delivered to a target cell by delivering to the cell an expression vector encoding the miRNA inhibitors or agonists. A vector is a composition of matter which can be used to deliver a nucleic acid of interest to the interior of a cell. Numerous vectors are known in the art, including, but not limited to, linear polynucleotides, polynucleotides associated with ionic or amphiphilic compounds, plasmids, and viruses. Thus, the term vector includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms expression construct, expression vector, and vector are used interchangeably to demonstrate the application of the invention in a general, illustrative sense, and are not intended to limit the invention.

In one embodiment, an expression vector for expressing a nucleic acid of the present invention comprises a promoter operably linked to a polynucleotide encoding the nucleic acid of the present invention. The phrase operably linked or under transcriptional control as used herein means that the promoter is in the correct location and orientation in relation to a polynucleotide to control the initiation of transcription by RNA polymerase and expression of the polynucleotide.

As used herein, a promoter refers to a DNA sequence recognized by the synthetic machinery of the cell, or introduced synthetic machinery, required to initiate the specific transcription of a gene.

Suitable promoters include, but are not limited to, RNA pol I, pol II, pol III, and viral promoters (e.g., human cytomegalovirus (CMV) immediate early gene promoter, the SV40 early promoter, and the Rous sarcoma virus long terminal repeat).

In certain embodiments, the promoter operably linked to a polynucleotide encoding a nucleic acid of the present invention can be an inducible promoter. Inducible promoters are known in the art and include, but are not limited to, the tetracycline promoter, the metallothionein IIA promoter, the heat shock promoter, the steroid/thyroid hormone/retinoic acid response elements, the adenovirus late promoter, and the inducible mouse mammary tumor virus LTR.

Methods of delivering expression constructs and nucleic acids to cells are known in the art and can include, by way of non-limiting example, calcium phosphate co-precipitation, electroporation, microinjection, DEAE-dextran, lipofection, transfection employing polyamine transfection reagents, cell sonication, gene bombardment using high velocity microprojectiles, and receptor-mediated transfection.

An aspect of the present invention provides a host cell comprising any herein-described nucleic acid of the present invention.

Another aspect of the present invention provides a method for inhibiting miR-22. The method comprising contacting miR-22 with a miR-22 inhibitory composition that is any herein-described nucleic acid of the present invention. The method may be in vitro or in vivo.

In another aspect, the present invention provides a pharmaceutical composition comprising any herein-described nucleic acid of the present invention and a pharmaceutically acceptable excipient or carrier.

Where clinical applications are contemplated, pharmaceutical compositions may be prepared in a form appropriate for the intended application. Generally, this will entail preparing compositions that are essentially free of pyrogens, as well as other impurities that could be harmful to humans or animals.

In one embodiment, a pharmaceutical composition comprises an effective dose of any herein-described nucleic acid of the present invention. An effective dose is an amount sufficient to affect a beneficial or desired clinical result. An effective dose may be from about 1 mg/kg to about 100 mg/kg, about 2.5 mg/kg to about 50 mg/kg, or about 5 mg/kg to about 25 mg/kg. The precise determination of what would be considered an effective dose may be based on factors individual to each patient, including their size, age, type of metabolic disorder, and nature of inhibitor or agonist (non-limiting examples include antagomir, expression construct, antisense oligonucleotide, polynucleotide duplex, etc.). Therefore, dosages can be readily ascertained by those of ordinary skill in the art from this disclosure and the knowledge in the art. For example, doses may be determined with reference Physicians' Desk Reference, 66th Edition, PDR Network; 2012 Edition (Dec. 27, 2011), the contents of which are incorporated by reference in its entirety.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the any herein-described nucleic acid of the present invention. Commercially available fat emulsions that are suitable for delivering the nucleic acids of the disclosure to adipose tissues (e.g., adipocytes) include INTRALIPIDO, LIPOSYN®, LIPOSYN® II, LIPOSYN® III, Nutrilipid, and other similar lipid emulsions. A colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and International Publication No. WO 03/093449, which are herein incorporated by reference in their entireties.

One will generally desire to employ appropriate salts and buffers to render delivery vehicles stable and allow for uptake by target cells. Aqueous compositions of the present invention comprise an effective amount of the delivery vehicle comprising any herein-described nucleic acid of the present invention (e.g., liposomes or other complexes or expression vectors) dissolved or dispersed in a pharmaceutically acceptable carrier or aqueous medium. The phrases pharmaceutically acceptable or pharmacologically acceptable refer to molecular entities and compositions that do not produce adverse, allergic, or other untoward reactions when administered to an animal or a human. As used herein, pharmaceutically acceptable carrier includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or polynucleotides of the compositions.

The pharmaceutical forms, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating any herein-described nucleic acid of the present invention in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions may be administered in a manner compatible with the dosage formulation and in such amount as is therapeutically effective.

EXAMPLES

In order that the invention disclosed herein may be more efficiently understood, examples are provided below. It should be understood that these examples are for illustrative purposes only and are not to be construed as limiting the invention in any manner.

Example 1: Design of LNA-Modified AntimiR-22 Oligonucleotides

All the LNA modified anti-miR-22 oligonucleotides are useful in both human and mouse. Host gene showed a 49% complementarity between human and mouse and LNA anti HG-miR-22 works predominately in human.

The oligonucleotides were designed to cover the seed sequence, contain between 8 nt and 20 nt in length, have a length-specific fraction of LNAs allowed and as high a binding affinity to miR-22 as possible (See FIG. 1, and FIG. 2A, FIG. 2B, and FIG. 2C).

Design elements included at least 2 LNA modifications at the end of the oligonucleotide. Further design elements included no more than 4 LNA modifications in a row. Further still design elements included no more than 3 unmodified residues in a row.

Figure 3A:
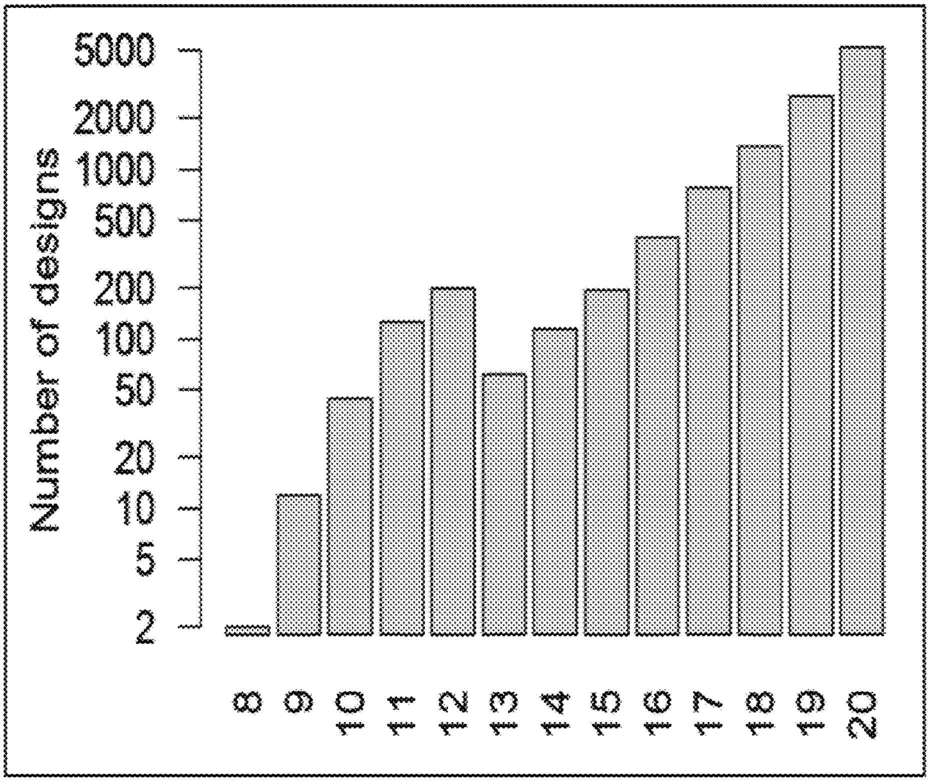
FIG. 3A and FIG. 3B show the generation of possible anti-miR designs in silico (11228) and predict properties to select most optimal anti-miR-22 designs (8-18 nt in length). SEQ ID NO: 11, SEQ ID NO: 2, SEQ ID NO: 7 to SEQ ID NO: 10, SEQ ID NO: 12, SEQ ID NO: 13, and SEQ ID NO: 1 are shown, moving from top to bottom of the legend of FIG. 3B.
Figure 3B:
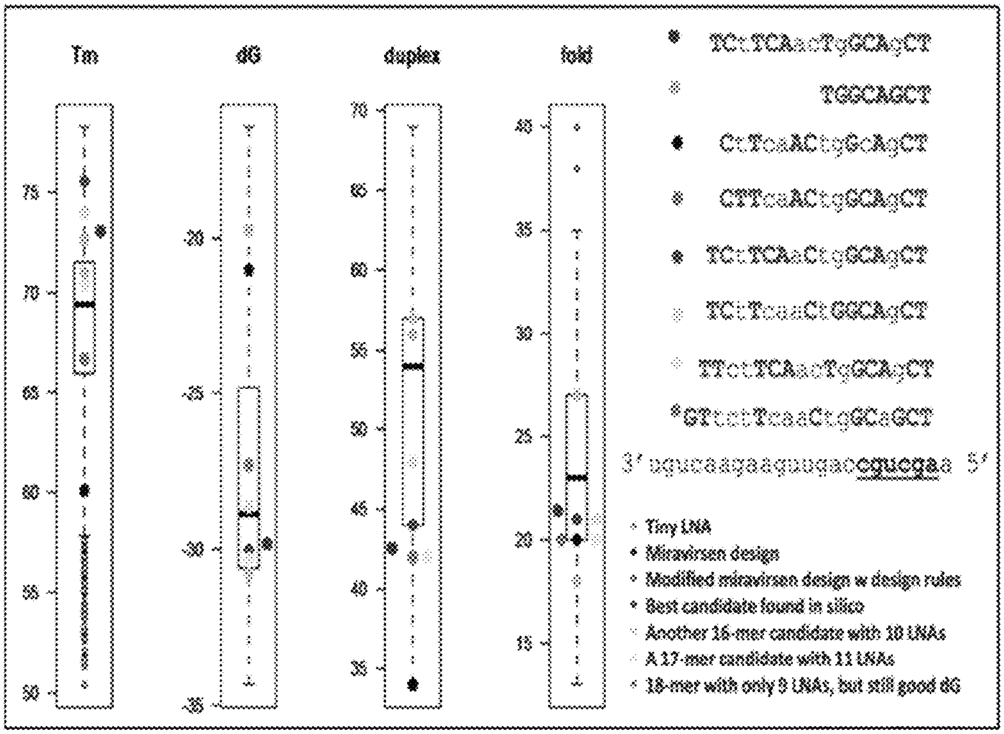

The oligonucleotides were designed to bind to miR-22 with sufficient affinity to inhibit it. Also, the oligonucleotides were designed to have limited or no self-binding affinity (e.g. no or limited duplex or fold structures). See FIG. 3A and FIG. 3B.

In the below sequences, capital letters are LNA-modified and lower-case letters are unmodified; the orientations for the miR-22 (SEQ ID NO: 1) and for the anti-miR-22 oligonucleotides (SEQ ID NO: 2 and SEQ ID NO: 7 to SEQ ID NO: 13) are orientated 5' to 3'. FIG. 1 shows the anti-miR-22 oligonucleotides orientated 3' to 5' as they would be when hybridizing to miR-22. The oligonucleotides of SEQ ID NO: 14 and SEQ ID NO: 15, orientated 5' to 3', are scrambled sequences and do not hybridize to the miR-22 (SEQ ID NO: 1).

```
                                        (SEQ ID NO: 1)
hsa-miR-22  AAGCUGCCAGUUGAAGAACUGU

                                        (SEQ ID NO: 2)
CRM0008     TGGCAGCT

                                        (SEQ ID NO: 7)
CRM0009     CtTcaACtgGcAgCT

                                        (SEQ ID NO: 8)
CRM0010     CTTcaACtgGCAgCT

                                        (SEQ ID NO: 9)
CRM0011     TCtTCAaCtgGCAgCT

                                       (SEQ ID NO: 10)
CRM0012     TCtTcaaCtGGCAgCT

                                       (SEQ ID NO: 11)
CRM0013     TCtTCAacTgGCAgCT

                                       (SEQ ID NO: 12)
CRM0014     TTctTCAacTgGCAgCT
```

-continued

```
                                       (SEQ ID NO: 13)
CRM0015     GTtctTcaaCtgGCaGCT

                                       (SEQ ID NO: 14)
CRM0016     CGaATAgTtaGTAgCG

                                       (SEQ ID NO: 15)
CRM0017     FAM labelled-CGaATAgTtaGTAgCG
```

Example 2: Inhibition of miR-22

The ability of the oligonucleotides of Example 1 to inhibit miR-22 was assessed.

The sequences were validated in an assay by optimization of protocol for LNA assisted uptake (Lipo200 transfection), an adherent cell line, FAM labeled LNA was used and the biological effect validated by Identifying the most potent anti-miR-22 in adherent cell line assisted and un-assisted uptake (analysis of miR-22 level pre and post treatment and TET2 activity and protein level). The aim was to use the anti-miR in a mouse model with the most potent anti-miR for use for in-vivo treatment, see FIG. 3A, FIG. 3B, FIG. 4, FIG. 5, FIG. 6, and FIG. 7 for confirmation results.

Figures 4A, 4B:
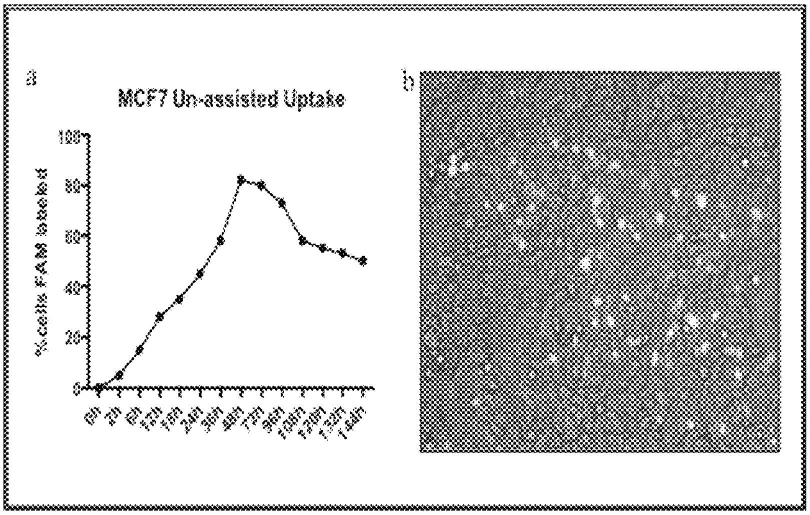
FIG. 4 shows unassisted uptake in MCF7 of a FAM-labeled LNA.

FIG. 4 reports the data obtained in MCF7 cells, demonstrating the capability of the tested LNA to enter into the cells.

Figure 5:
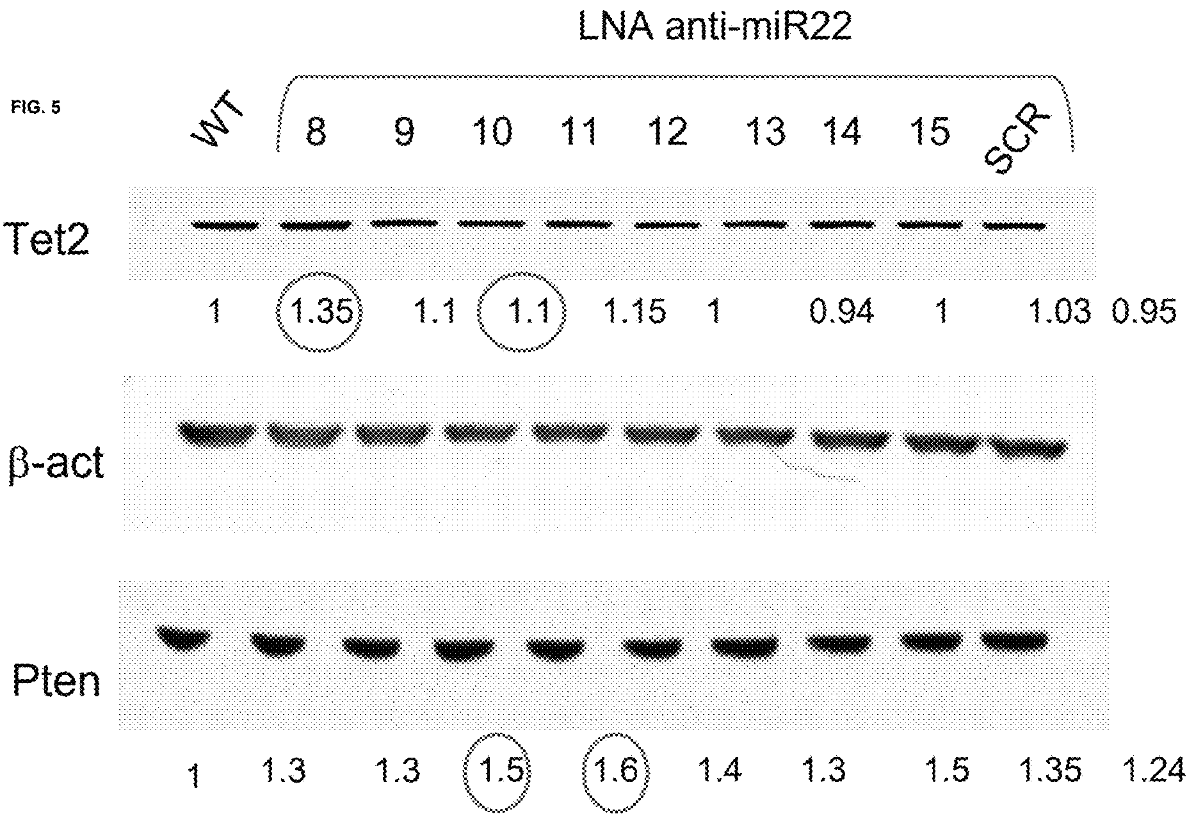
FIG. 5 is a western blot showing the validation of anti-miR-22 LNAs in MCF7 cells.

In FIG. 5, MCF7 cells were treated with different LNA. A single dose of LNA was added to the medium in the presence of Lipofectamine, according to manufacturer's recommendation, at a final concentration of 10 nM. After 48 h cells were harvested and protein level was analyzed by Western Blot. TET2 and PTEN, two bona-fide targets of miR-22, protein level were checked and quantified using ImageJ software suite, using (3-Actin as internal loading control.

The conclusion from this experiment is the observed capability of the claimed LNA #10 to increase both the two indicators of a miR-22 inhibition, a capability surprising not observed with the other tested LNAs.

Figure 6A:
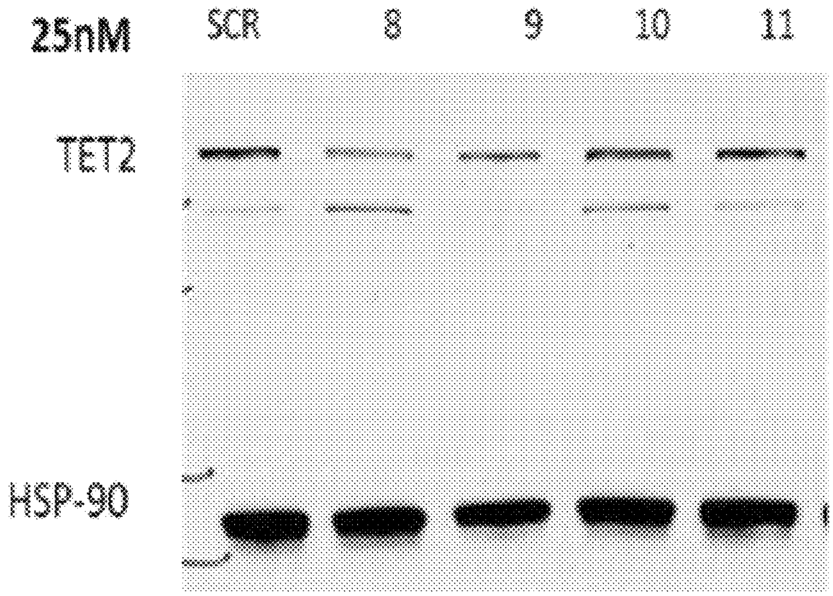
FIG. 6A, FIG. 6B, and FIG. 6C show unassisted uptake of LNA-modified anti-miR-22 oligonucleotides in MCF7 cells affecting target protein levels.
Figure 6B:
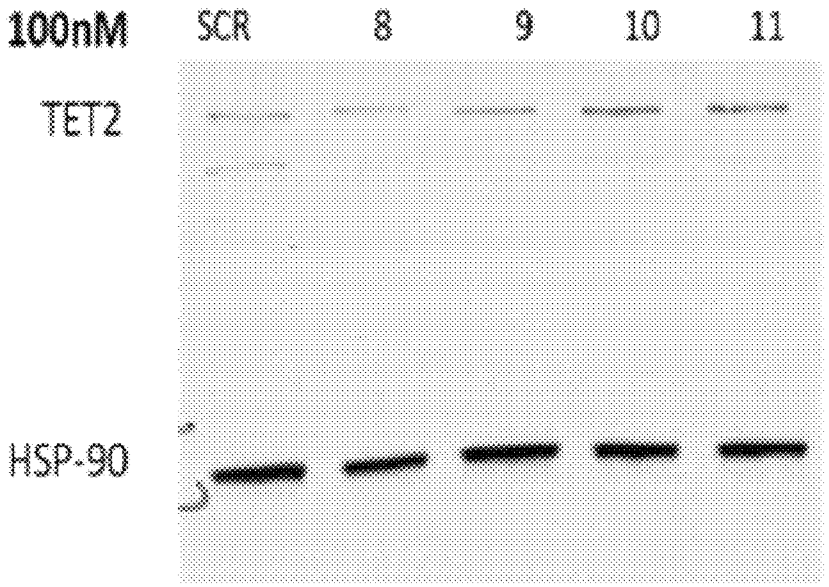
Figure 6C:
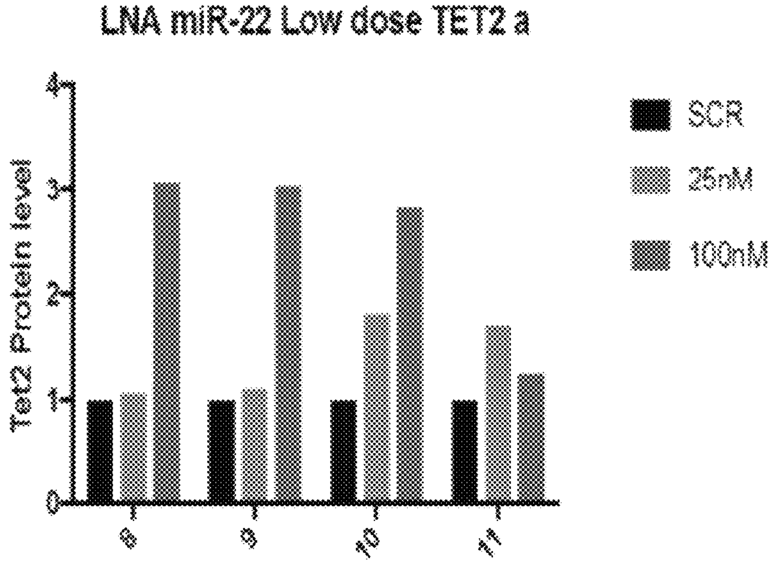

The surprising advantageous effect obtained when using LNA #10 is confirmed with the experiment reported in FIG. 6. Also in this experimental setting, MCF7 cells are used and exposed to a selection of the LNA library composed by the top 4 compounds that performed better in de-repressing PTEN and TET2 protein level in the assisted uptake set of experiments, i.e. LNA #8, LNA #9, LNA #10 and LNA #11. The LNA was added to the medium in absence of any reagent that could facilitate transfection at a final concentration of 10 nM, 25 nM and 100 nM. After 48 h, cells were harvested and protein level was analyzed by Western Blot. TET2 and PTEN, two bona-fide targets of miR-22, protein level were checked and quantified using ImageJ software suite, using HSP-90 as internal loading control.

LNA #10 was able to increase both TET2 and PTEN level in this setting, too. Moreover, LNA #10 is the only oligonucleotide tested capable to elicit an effect in a dose-dependent manner, being active already at the lowest concentration tested. As shown in FIG. 6, panel C, LNA #8 and LNA #9 do not show any effect at 25 nM, wherein LNA #11, although effective at 25 nM, does not show efficacy at 100 nM and this is indicative of an unspecific effect.

Figure 7:
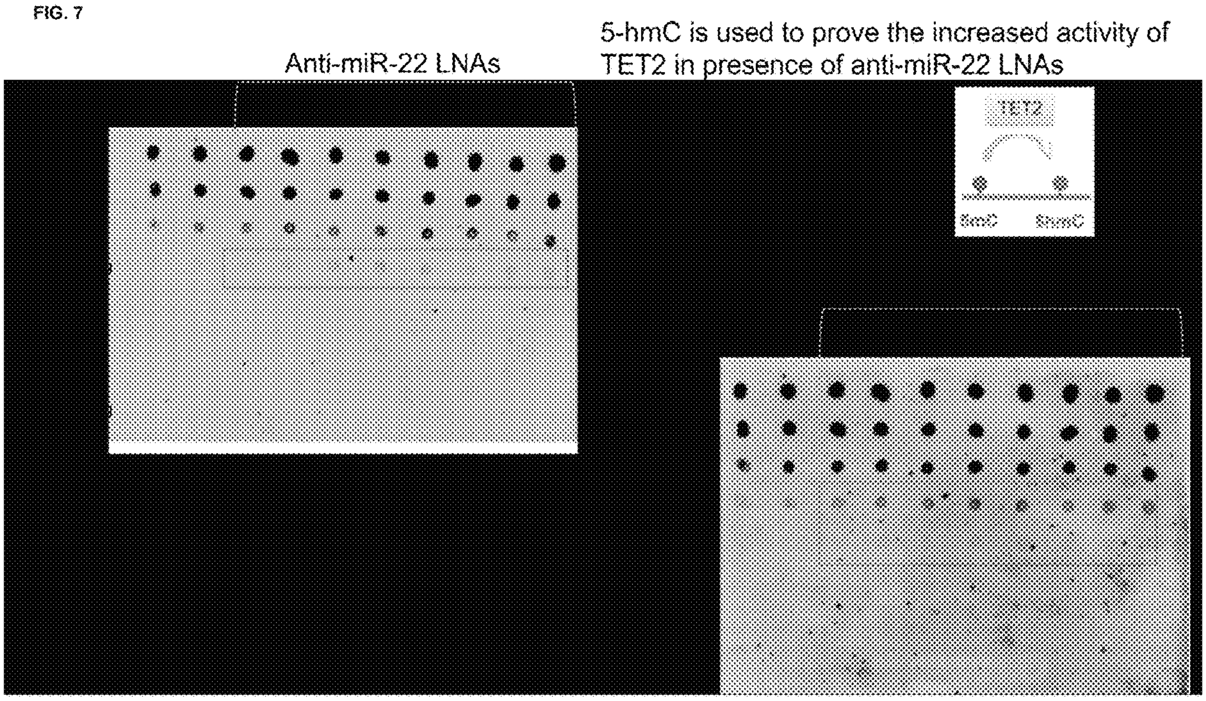
FIG. 7 shows a pair of dot-blot images demonstrating that treatment with LNA-modified antimiR-22 oligonucleotides increase the level of 5-hmC in MCF7 cells.

A functional experiment is shown up in FIG. 7. Dot blot of DNA from MCF7 and PC3 cells treated with the entire LNA library against miR-22 has been performed to test the amount of 5hmC (5-hydroxymethylcytosine) in the different condition. Briefly, after cells were treated with the LNAs at the final concentration of 25 nM for 48 h, DNA was extracted and quantified. Serial dilution of DNA were spotted on nitrocellulose, starting from 500 ng to 6.25 ng. Nitrocellulose was blocked and then incubated with an anti-5hmC antibody, able to recognize only the cytosines that present and hydroxy-methyl group, as a result of TET2 activity. Treatment with LNA #10 results in the highest increase level of 5hmC, wherein only when using LNA #10 a signal is detected at 32.25 ng, too. The results are indicative of the fact that TET, a miR-22 bona-fide target, is increased by LNA #10 not only at the mRNA and protein level but also in its functionality.

Further validation of the ability of the constructs of Example 1 to inhibit miR-22 was assessed in vivo in an obesity model.

Figure 8:
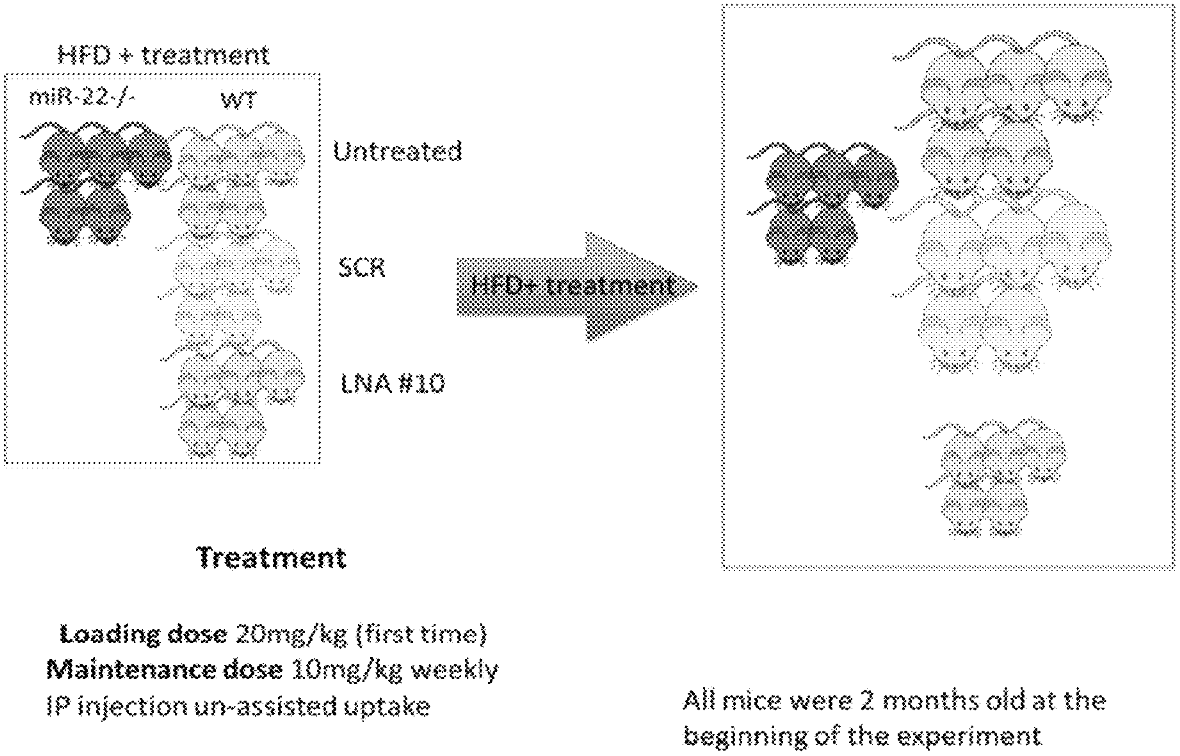
FIG. 8 shows in vivo experimental planning and conditions for miR-22−/− and WT mice on HFD following transfection of Vehicle (VCH), Scramble Control oligonucleotide (SCR) and Locked Nucleic Acid-modified anti-mir-22 compound (LNA).
Figure 9:
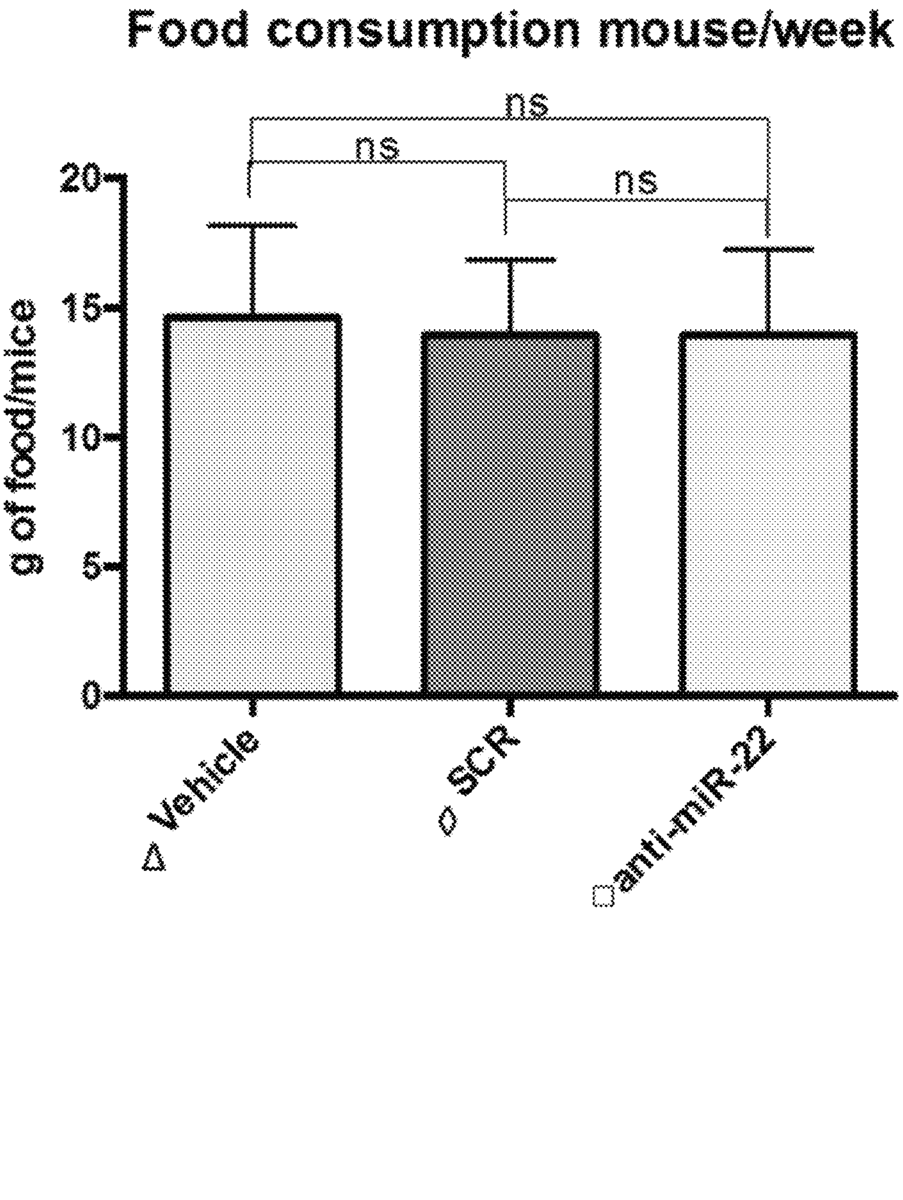
FIG. 9 is a bar graph showing that there is no difference between treated and non-treated mice in food consumption for (Δ) Vehicle, (♦) SCR, (■) anti-miR-22.
Figure 10A:
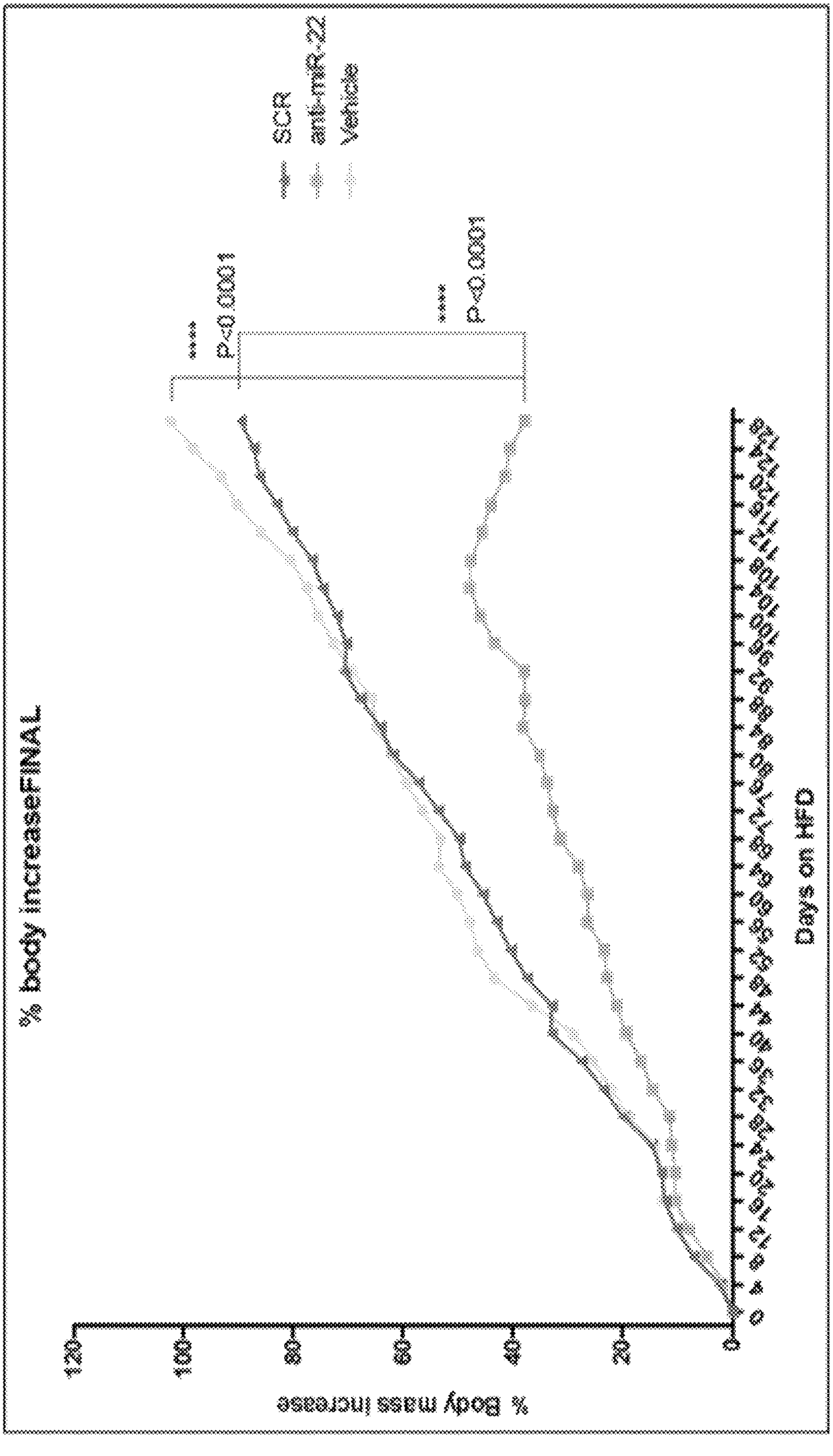
FIG. 10A and FIG. 10B are line graphs showing results from in vivo pharmacological inhibition of miR-22 preventing mice from becoming obese.
Figure 10B:
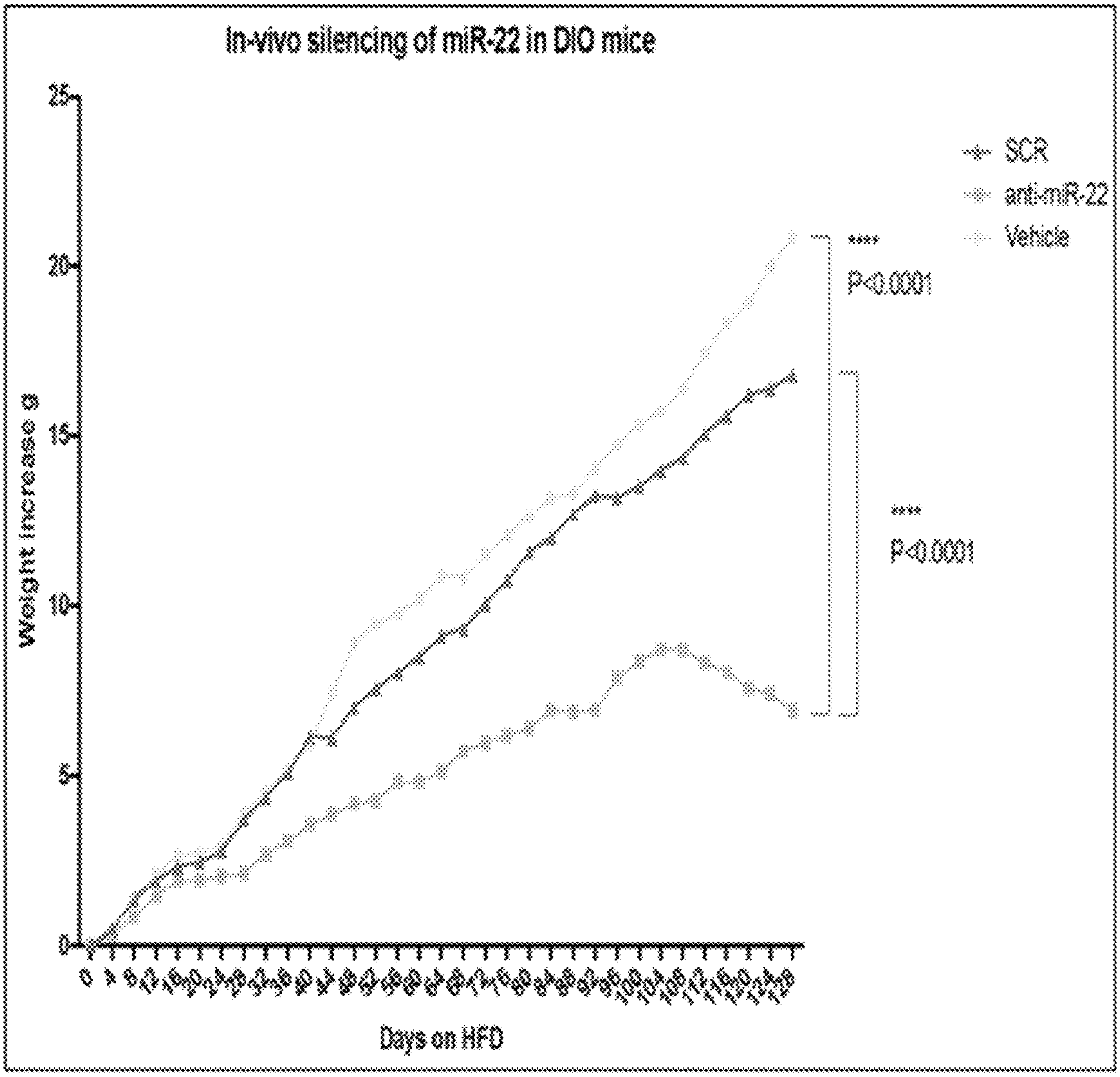

In an in vivo experimental planning for prevention, see FIG. 8, 2 months old miR-22−/− and WT on HFD were transfected with Vehicle (VCH), Scramble Control RNA (SCR) and a Locked Nucleic Acid (LNA) of Example 1 and treated with a Loading dose 20 mg/kg (first time) and a Maintenance dose 10 mg/kg weekly IP injection un-assisted uptake. There was no difference between treated and non-treated mice in food consumption, see FIG. 9. In vivo pharmacological inhibition of miR-22 prevented mice from becoming obese. See FIG. 10A and FIG. 10B.

Figure 11:
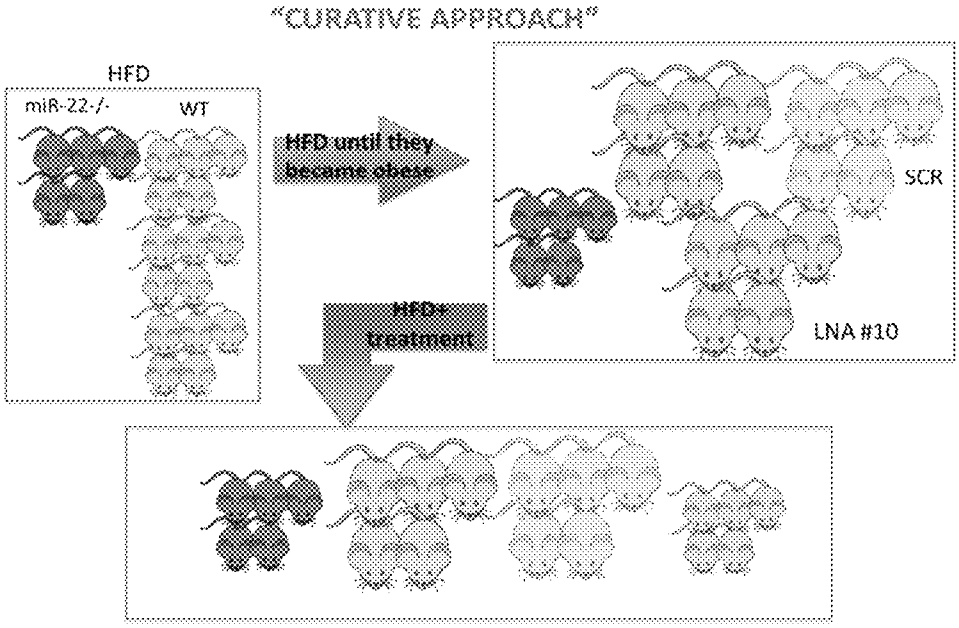
FIG. 11 are images showing treatment of miR-22−/− and WT mice on a HFD treated with an anti-miR-22-LNA, SCR and a VHL and placed on a second HFD regimen.
Figure 12:
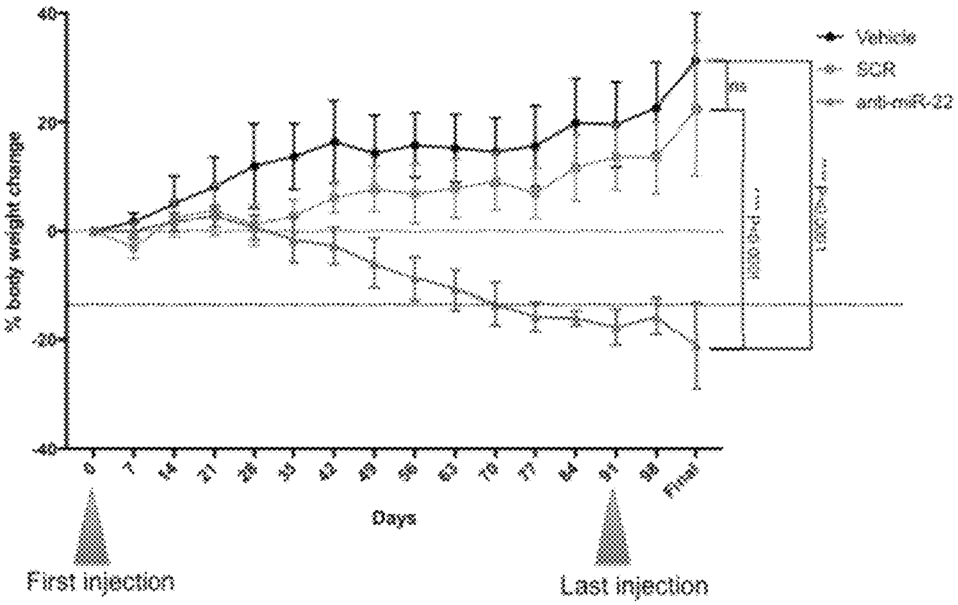
FIG. 12 is a line graph showing the results of the curative approach whereby there is a significant reduction in body weight in obese mice fed with a HFD. After 3½ months of treatment, a significant reduction in body weight was observed in obese mice (average weight >40 g) and fed with HFD. Mice were sacrificed, tissue collected, RNA from livers used for RNAseq.

FIG. 11 is a pictorial of a curative approach showing miR-22−/− and WT mice on a HFD treated with an anti-miR-22-LNA, SCR and a VHL and placed on a second HFD regimen. As shown in FIG. 12, a construct of Example 1 inhibited miR-22, as evidenced by weight loss.

Figure 13:
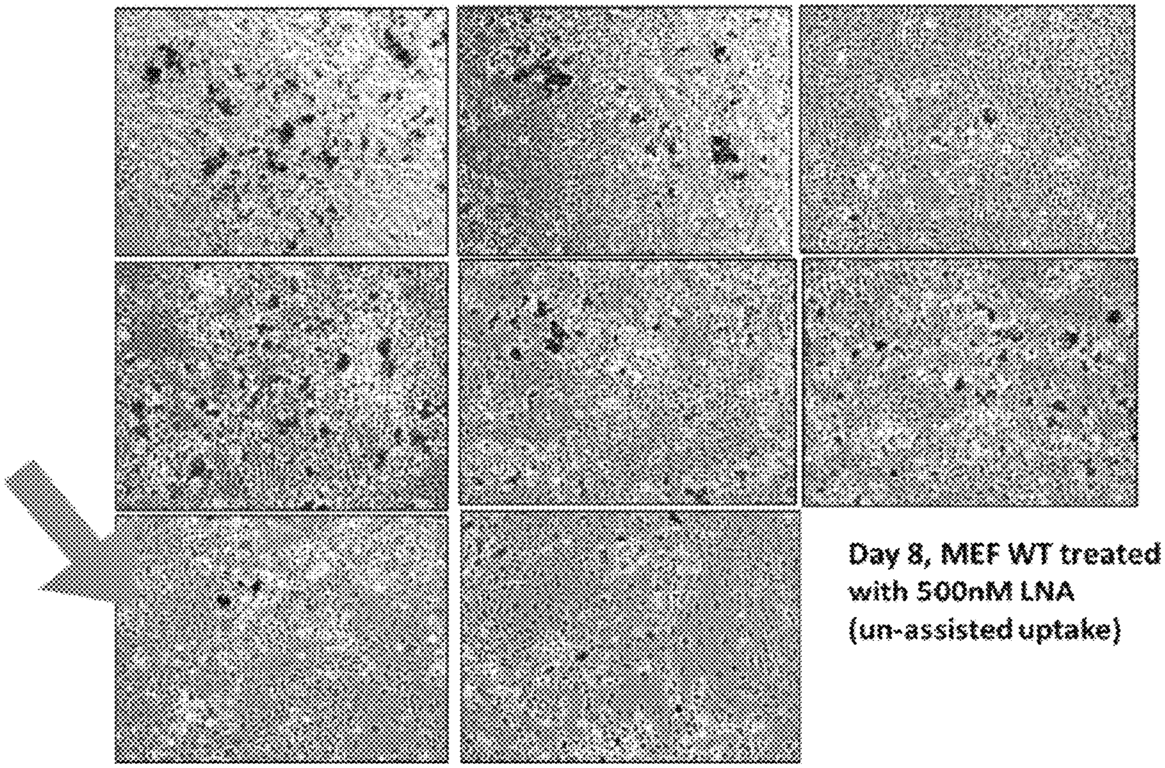
FIG. 13 is an Oil-Red-O staining showing that pharmacological inhibition of miR-22 is effective in impairing MEFs adipocytic differentiation of mesenchymal stem cells.
Figure 14A:
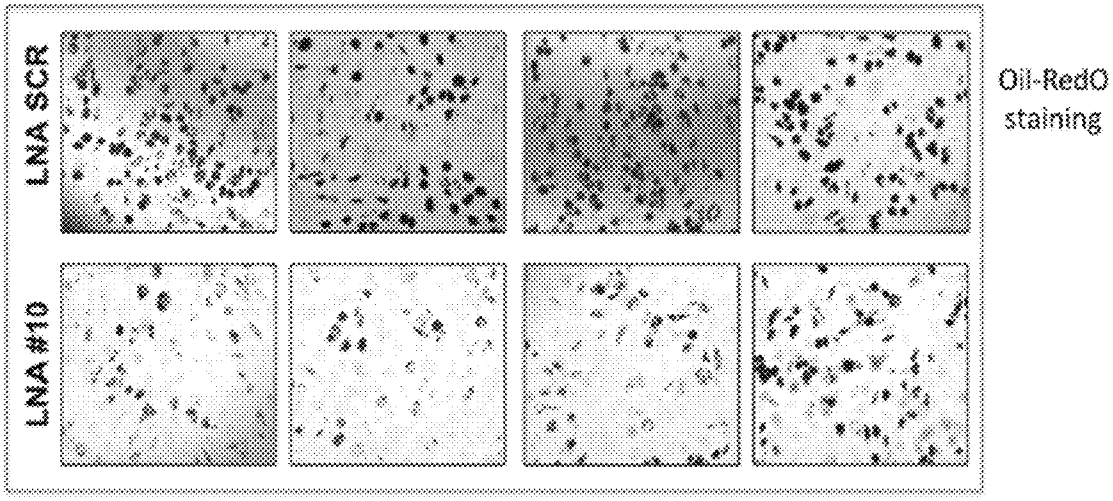
FIG. 14A is an Oil-Red-O staining, and FIG. 14B a bar graph showing the results of anti-miR-22 treatment in Human Primary Mesenchymal cells cultured in adipocyte differentiation media for 2 weeks with or without LNA anti-miR-22 by un-assisted uptake of the antimir-22 oligonucleotide at 500 nM (added every 2 days).
Figure 14B:
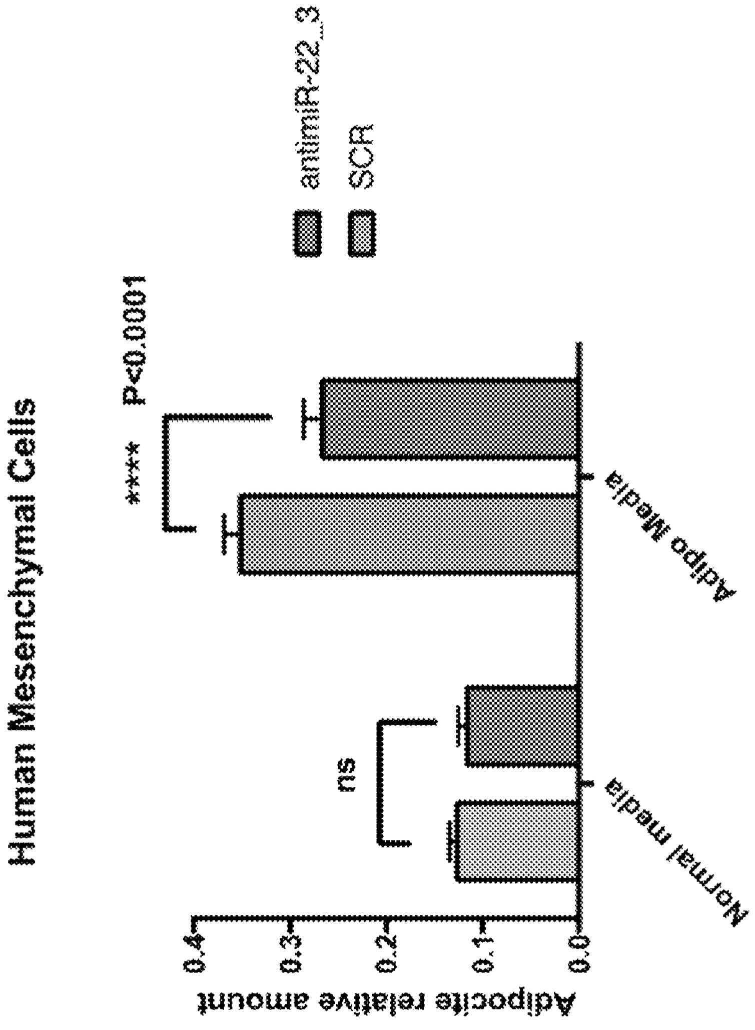
In FIG. 14B, the data in the right bar in each bar graph is for the with LNA #10-treated cells.
Figure 15:
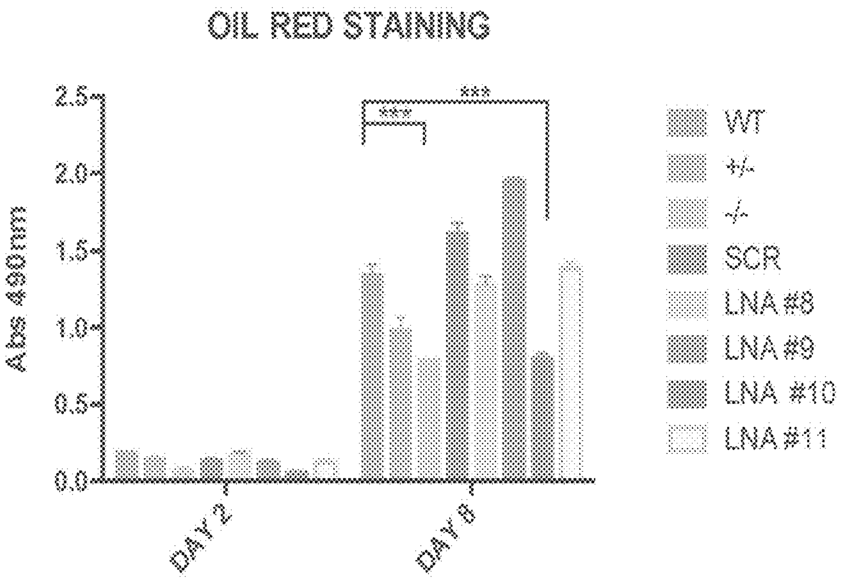
FIG. 15 is a bar graph showing that pharmacological inhibition of miR-22 is effective in impairing adipocytic differentiation of human mesenchymal stem cells. The order of data in the bar graphs, when reading from left to right corresponds with the legend (at the right of the graph) when reading from top to bottom.
Figure 16A:
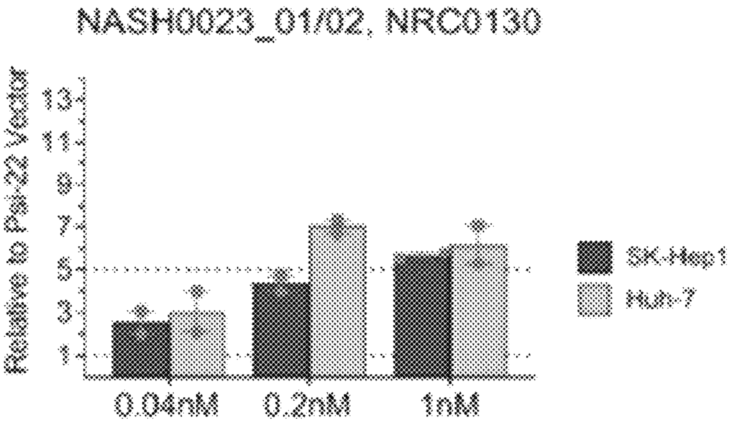
FIG. 16A, FIG. 16B, FIG. 16C, FIG. 16D, FIG. 16E, and FIG. 16F each show a bar graph of the in vitro potency of the indicated antimiR-22 oligonucleotides.
Figure 16B:
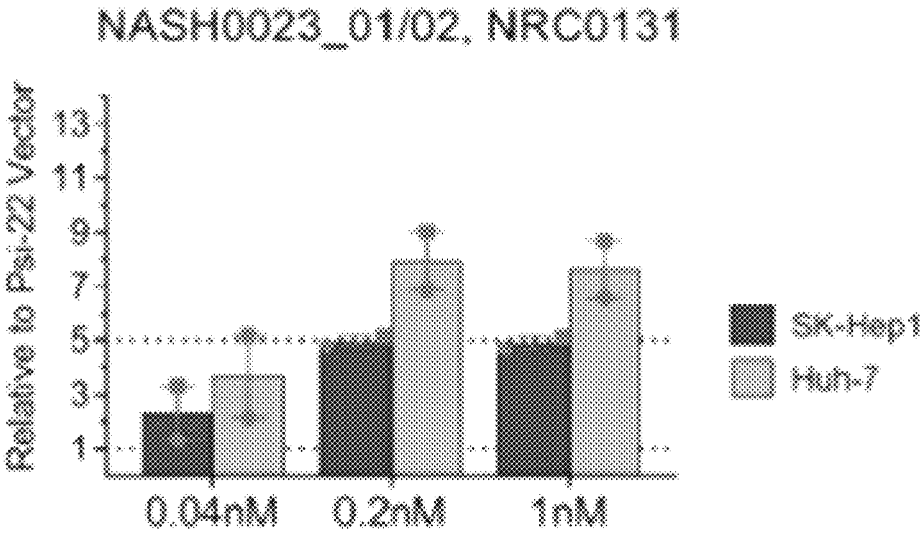
Figure 16C:
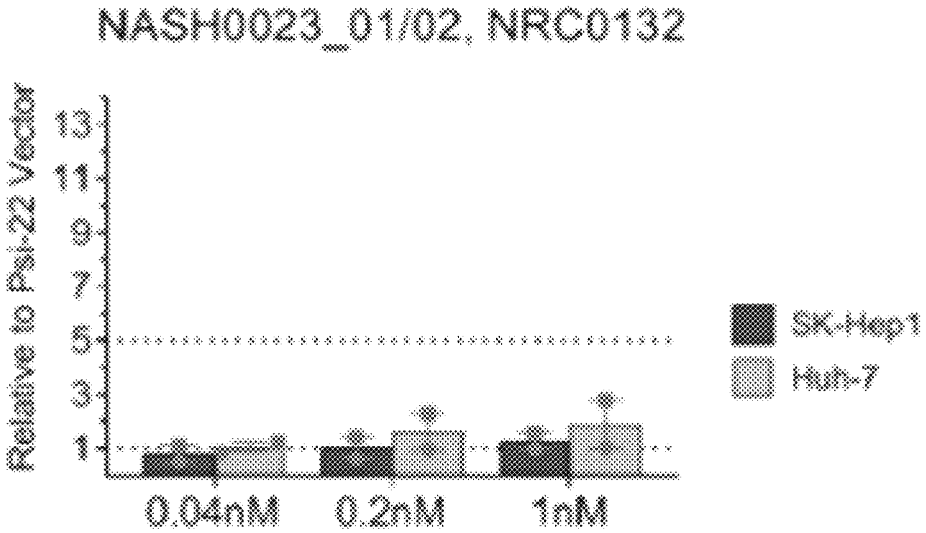
Figure 16D:
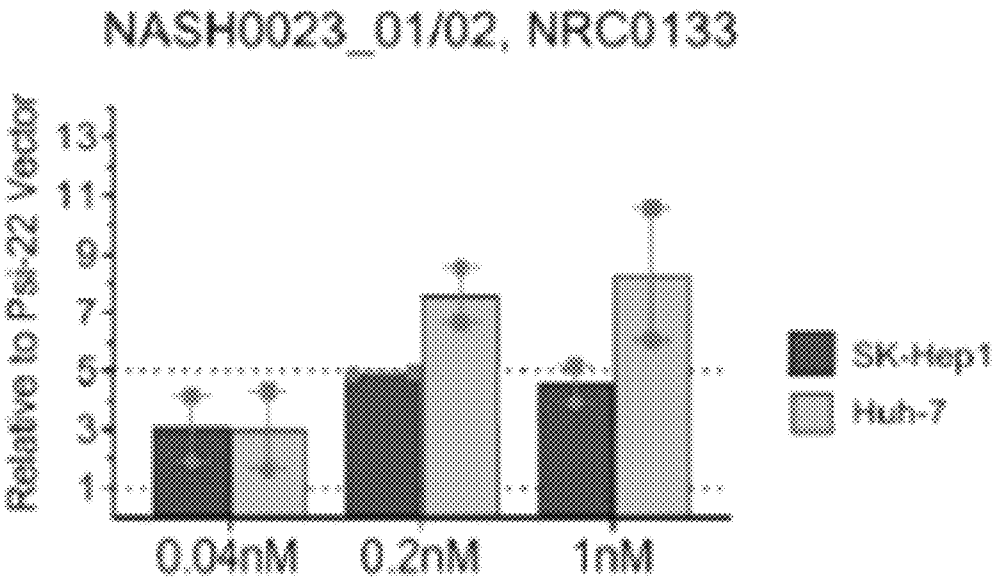
Figure 16E:
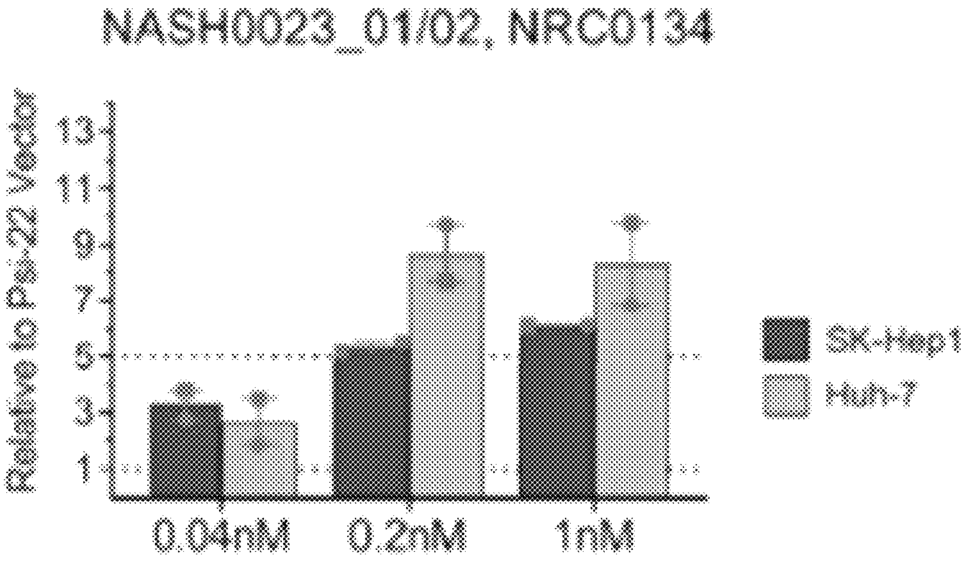
Figure 16F:
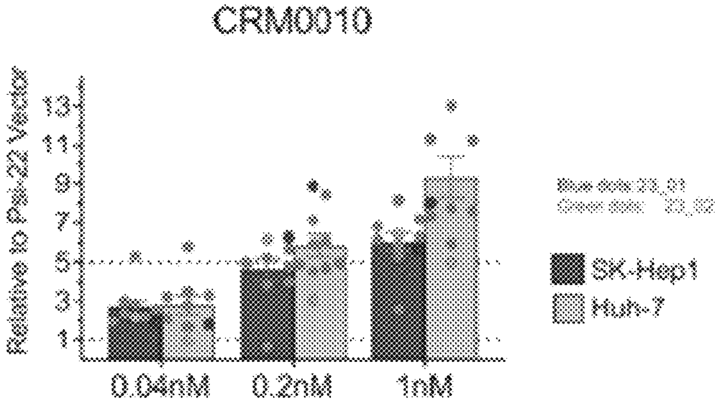

Further evidence of miR-22 inhibition was seen in Oil-Red-O staining experiments that show impairing MEFs adipocytic differentiation. FIG. 13 shows that pharmacological inhibition of miR-22 with the constructs of Example 1 is effective in impairing MEFs adipocytic differentiation. FIG. 14A is an Oil-Red O staining, and a bar graph (FIG. 14B) showing that anti-miR-22 treatment in Human Primary Mesenchymal cells cultured in Adipo differentiation media for 2 weeks with or without LNA anti-miR-22. Un-assisted uptake 500 nM (LNAs added every 2 days). In FIG. 14B, the data in the right (red) bars in each bar graph is for the with LNA #10-treated cells. FIG. 15 is a bar graph showing that pharmacological inhibition of miR-22 is effective in impairing MEFs adipocytic differentiation. The order of data in the bar graphs, when reading from left to right corresponds with the legend (at the right of the graph) when reading from top to bottom. The number of LNAs corresponds to Example 1 above.

Accordingly, the nucleic acid constructs of Example 1 are effective in inhibiting miR-22.

Example 3: Design of Additional LNA-Modified AntimiR-22 Oligonucleotides

All the LNA-modified anti-miR-22 oligonucleotides are useful in both human and mouse. Host gene showed a 49% complementarity between human and mouse and LNA anti HG-miR-22 works predominately in human.

The LNA-modified anti-miR-22 oligonucleotides were designed to cover the seed sequence, contain between 17 nt and 20 nt in length, have a length-specific fraction of LNAs allowed and as high a binding affinity to miR-22 as possible. Design elements included at least 8 LNA modifications in the oligonucleotides. Further design elements included no more than 4 LNA modifications in a row. Further still design elements included no more than 3 unmodified residues in a row.

The oligonucleotides were designed to bind to miR-22 with sufficient affinity to inhibit it.

In Table 1, capital letters are LNA-modified and lower-case letters are unmodified; the orientations for the miR-22 (SEQ ID NO: 1) and for the anti-miR-22 oligonucleotides (SEQ ID NO: 21 and SEQ ID NO: 16 to SEQ ID NO: 20) are orientated 5' to 3'. One PS (Phosphorothioate) linkage has been substituted with one PO (Phosphine Oxide) linkage in each antimiR-22 compound. Phosphorothioate linkages are denoted by * in Table 1.

For comparative purposes, CRM0010, alternatively named LNA-10, or RES-010 has been included among the Oligos.

TABLE 1

| Oligo-Id | Sequence (5'-3') | SEQ ID |
|---|---|---|
| NRC0130 | G*T*T*c*t*T*c*AA*c*T*G*g*C*A*g*C*T | SEQ ID NO: 16 |
| NRC0131 | G*T*t*c*T*TC*a*A*c*T*G*g*C*a*g*C*T | SEQ ID NO: 17 |
| NRC0132 | G*T*t*c*T*T*c*A*a*C*T*G*g*CA*g*C*T | SEQ ID NO: 18 |
| NRC0133 | G*T*t*C*t*T*c*A*a*CT*g*g*c*A*g*C*I | SEQ ID NO: 19 |
| NRC0134 | G*T*t*c*T*T*c*A*a*C*t*g*G*CA*g*C*T | SEQ ID NO: 20 |
| CRM0010 | C*T*T*c*a*A*C*t*g*G*C*A*g*C*T | SEQ ID NO: 21 |

Example 4: Assessment of In Vitro Potency of AntimiR-22 Oligonucleotide Compounds Using a miR-22 Luciferase Reporter Assay Cell Lines The human liver cancer cell lines SK-Hep-1 and Huh-7D12 were purchased from the European Collection of Authenticated Cell Cultures (ECACC, UK). SK-Hep-1 cell line was cultured in EMEM (Sigma) supplemented with 10% FBS (Sigma), 1% Glutamine (2 mM; Sigma), 1% P/S (Sigma), 1% NEAA (Sigma) and 1% sodium pyruvate solution (1 mM NaP, sterile-filtered, Sigma). Huh-7D12 cells were cultured in Dulbecco's Modified Eagle Medium (DMEM; Sigma) supplemented with 10% FBS (Sigma), 1% Glutamine (2 mM; Sigma) and 1% P/S (Sigma). All cell cultures were incubated in 5% CO2 at 37° C. Cell counts were performed with Countess II FL Automated Cell Counter (Thermo Fisher Scientific).

Generation of the miR-22 Luciferase Reporter Plasmid

The miR-22 perfect match (PM) target site reporter was generated by cloning the PM site of miR-22 (1×PM) into the multiple cloning site downstream of renilla luciferase (Rluc) in the PsiCHECK™2 vector (C8021, Promega). Briefly, a PM primer pair including Xhol (5') and Notl (3') overhangs was generated using the following primers: miR-22 PM Sense; CTCGAGACAGTTCTT-CAACTGGCAGCTTGCGGCCG (SEQ ID NO: 22), miR-22 PM Antisense; GGCCGCAAGCTGCCAGTT-GAAGAACTGTC (SEQ ID NO: 23). After annealing of the primers (10 min, 85° C. followed by cooling 1° C./min to 4° C.), the psiCHECK™-2 vector (Promega, C8021) was digested with Notl (NEB R0189S) and XhoI (NEB R0146S) in NEB-buffer 3.1 (NEB B7203S) for 2 hours, 37° C. The enzymes were heat-inactivated for 15 min, 65° C. and the plasmid was purified using the Plasmid DNA purification Nucleospin Quickpure (Fisher Scientific 11902362). The plasmid and the PCR fragment were ligated for one hour at room temperature using a T4 DNA Ligase (NEB M0202S). The ligation mix was transformed into One Shot TOP10 Chemically Competent *E. coli* cells (C4040-03, Invitrogen) and spread on LB-plates (LB Broth with AGAR (Miller) Sigma-Aldrich L3147) with 50 μg/mL Ampicillin (Ampicillin-Sigma-Aldrich A5354) and incubated at 37° C. overnight. Colonies were picked in 2 ml LB+ampicillin (LB Broth (Miller) Sigma-Aldrich L3522) and grown by shaking overnight at 37° C. To verify the inserts of the selected colonies we used a common forward primer (CTATTGTCGAGGGAGCTAAGAAGT (SEQ ID NO: 24), located in the hluc gene) and an insert specific reverse primer (miR-22 reverse; CGCAAGCTGCCAGTTGAAGAACTG (SEQ ID NO: 25)) to amplify (AmpliTaq Gold™ DNA Polymerase, Applied Biosystems, 4311806) the specific fragment of interest in a 1.5% agarose gel. The plasmids were purified using QuickLyse Miniprep (Qiagen 27405) and then sequenced at Eurofins Genomics using the following primers: psiCHECK™2 common forward; CTATTGTCGAGGGAGCTAAGAAGT (SEQ ID NO: 26), psiCHECK™2 common reverse; GCGTCAGACAAACCCTAACCA (SEQ ID NO: 27). Finally, the confirmed miR-22 luciferase reporter plasmid was grown overnight in 50 ml LB+Amp followed by purification using Endofree Plasmid Maxi kit (Qiagen 12362).

Luciferase Reporter Assays

Transfection of antimiR-22 oligonucleotides and the miR-22 luciferase reporter plasmid (PsiCHECK 2-miR-22 PM) was performed in SK-Hep-1 and Huh-7D12 using Lipofectamine 2000 (Thermo Scientific, 11668-019). Briefly, cells were plated in collagen-coated 96-wells (Corning® 96 Well White Polystyrene Microplate; Sigma CLS3610-48EA) one day prior to transfection (80-90% confluent at time of transfection). Cells were washed once in OptiMEM (Thermo Scientific, 51985-026) before addition of Lipofectamine mixture (SK-Hep-1: 5 μg/mL, Huh-7D12: 2.5 μg/mL). The cells were incubated 7 min at RT before addition of the plasmid (0.0001 μg/μL) and the antimiR-22 oligonucleotides (1.0, 0.2, or 0.04 nM final concentration). The cells were incubated 4 hours at 37° C., 5% $CO_2$ before a single wash with OptiMEM. After addition of 75 μL culture medium, the cells were incubated overnight for 20 hours at 37° C., 5% $CO_2$. Luciferase activity (Firefly and Renilla) was measured using the Dual-Glo Luciferase Assay System (Promega, E2920) following the manufacturer's protocol. After background subtraction, the renilla activity was normalized to firefly within each well (renilla/firefly). The potency of the antimiR-22 oligonucleotides was compared to that of CRM0010. Data are reported in FIG. 16A, FIG. 16B, FIG. 16C, FIG. 16D, FIG. 16E, and FIG. 16F. NRC0131, NRC0133 and NRC0134 appear to be more potent at 0.2 nM concentration compared to CRM0010.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any way.

What is claimed is:

1. A miR-22 inhibitory composition comprising a nucleic acid having a sequence selected from the group consisting of: G*T*t*c*T*TC*a*A*c*T*G*g*C*a*g*C*T (SEQ ID NO: 17), G*T*t*C*t*T*c*A*a*CT*g*g*c*A*g*C*T (SEQ ID NO: 19), and G*T*t*c*T*T*c*A*a*C*t*g*G*CA*g*C*T (SEQ ID NO: 20), wherein the capital letters are LNA modifications, the lower case are unmodified, the symbol * denotes PS linkages, and the absence of the * symbol denotes PO linkages.

2. A pharmaceutical composition comprising the nucleic acid of claim 1, and a pharmaceutically acceptable excipient or carrier.

3. A vector or plasmid comprising a sequence encoding the nucleic acid molecule according to claim 1.

4. A host cell comprising the nucleic acid of claim 1.

5. A method for inhibiting miR-22 comprising contacting miR-22 with a miR-22 inhibitory composition of claim 1.

6. A method of treating obesity in a subject, the method comprising administrating the pharmaceutical composition according to claim 2 to the subject.

* * * * *

SEQUENCE LISTING

```
Sequence total quantity: 27
SEQ ID NO: 1           moltype = RNA  length = 22
FEATURE                Location/Qualifiers
source                 1..22
                       mol_type = genomic RNA
                       organism = Homo sapiens
SEQUENCE: 1
aagctgccag ttgaagaact gt                                          22

SEQ ID NO: 2           moltype =   length =
SEQUENCE: 2
000

SEQ ID NO: 3           moltype = DNA  length = 15
FEATURE                Location/Qualifiers
misc_feature           1..15
                       note = Synthetic Nucleic Acid
source                 1..15
                       mol_type = other DNA
                       organism = synthetic construct
SEQUENCE: 3
cttcaactgg cagct                                                  15

SEQ ID NO: 4           moltype = DNA  length = 16
FEATURE                Location/Qualifiers
misc_feature           1..16
                       note = Synthetic Nucleic Acid
source                 1..16
                       mol_type = other DNA
```

```
                       organism = synthetic construct
SEQUENCE: 4
tcttcaactg gcagct                                                  16

SEQ ID NO: 5           moltype = DNA  length = 17
FEATURE                Location/Qualifiers
misc_feature           1..17
                       note = Synthetic Nucleic Acid
source                 1..17
                       mol_type = other DNA
                       organism = synthetic construct
SEQUENCE: 5
ttcttcaact ggcagct                                                 17

SEQ ID NO: 6           moltype = DNA  length = 18
FEATURE                Location/Qualifiers
misc_feature           1..18
                       note = Synthetic Nucleic Acid
source                 1..18
                       mol_type = other DNA
                       organism = synthetic construct
SEQUENCE: 6
gttcttcaac tggcagct                                                18

SEQ ID NO: 7           moltype = DNA  length = 15
FEATURE                Location/Qualifiers
misc_feature           1..15
                       note = Synthetic Nucleic Acid
source                 1..15
                       mol_type = other DNA
                       organism = synthetic construct
SEQUENCE: 7
cttcaactgg cagct                                                   15

SEQ ID NO: 8           moltype = DNA  length = 15
FEATURE                Location/Qualifiers
misc_feature           1..15
                       note = Synthetic Nucleic Acid
source                 1..15
                       mol_type = other DNA
                       organism = synthetic construct
SEQUENCE: 8
cttcaactgg cagct                                                   15

SEQ ID NO: 9           moltype = DNA  length = 16
FEATURE                Location/Qualifiers
misc_feature           1..16
                       note = Synthetic Nucleic Acid
source                 1..16
                       mol_type = other DNA
                       organism = synthetic construct
SEQUENCE: 9
tcttcaactg gcagct                                                  16

SEQ ID NO: 10          moltype = DNA  length = 16
FEATURE                Location/Qualifiers
misc_feature           1..16
                       note = Synthetic Nucleic Acid
source                 1..16
                       mol_type = other DNA
                       organism = synthetic construct
SEQUENCE: 10
tcttcaactg gcagct                                                  16

SEQ ID NO: 11          moltype = DNA  length = 16
FEATURE                Location/Qualifiers
misc_feature           1..16
                       note = Synthetic Nucleic Acid
source                 1..16
                       mol_type = other DNA
                       organism = synthetic construct
SEQUENCE: 11
tcttcaactg gcagct                                                  16

SEQ ID NO: 12          moltype = DNA  length = 17
FEATURE                Location/Qualifiers
misc_feature           1..17
                       note = Synthetic Nucleic Acid
source                 1..17
```

-continued

```
                        mol_type = other DNA
                        organism = synthetic construct
SEQUENCE: 12
ttcttcaact ggcagct                                                   17

SEQ ID NO: 13           moltype = DNA  length = 18
FEATURE                 Location/Qualifiers
misc_feature            1..18
                        note = Synthetic Nucleic Acid
source                  1..18
                        mol_type = other DNA
                        organism = synthetic construct
SEQUENCE: 13
gttcttcaac tggcagct                                                  18

SEQ ID NO: 14           moltype = DNA  length = 16
FEATURE                 Location/Qualifiers
misc_feature            1..16
                        note = Synthetic Nucleic Acid
source                  1..16
                        mol_type = other DNA
                        organism = synthetic construct
SEQUENCE: 14
cgaatagtta gtagcg                                                    16

SEQ ID NO: 15           moltype = DNA  length = 16
FEATURE                 Location/Qualifiers
misc_feature            1..16
                        note = Synthetic Nucleic Acid
source                  1..16
                        mol_type = other DNA
                        organism = synthetic construct
SEQUENCE: 15
cgaatagtta gtagcg                                                    16

SEQ ID NO: 16           moltype = DNA  length = 18
FEATURE                 Location/Qualifiers
source                  1..18
                        mol_type = other DNA
                        organism = synthetic construct
SEQUENCE: 16
gttcttcaac tggcagct                                                  18

SEQ ID NO: 17           moltype = DNA  length = 18
FEATURE                 Location/Qualifiers
source                  1..18
                        mol_type = other DNA
                        organism = synthetic construct
SEQUENCE: 17
gttcttcaac tggcagct                                                  18

SEQ ID NO: 18           moltype = DNA  length = 18
FEATURE                 Location/Qualifiers
source                  1..18
                        mol_type = other DNA
                        organism = synthetic construct
SEQUENCE: 18
gttcttcaac tggcagct                                                  18

SEQ ID NO: 19           moltype = DNA  length = 18
FEATURE                 Location/Qualifiers
source                  1..18
                        mol_type = other DNA
                        organism = synthetic construct
SEQUENCE: 19
gttcttcaac tggcagct                                                  18

SEQ ID NO: 20           moltype = DNA  length = 18
FEATURE                 Location/Qualifiers
source                  1..18
                        mol_type = other DNA
                        organism = synthetic construct
SEQUENCE: 20
gttcttcaac tggcagct                                                  18

SEQ ID NO: 21           moltype = DNA  length = 15
FEATURE                 Location/Qualifiers
source                  1..15
                        mol_type = other DNA
```

-continued

```
                       organism = synthetic construct
SEQUENCE: 21
cttcaactgg cagct                                            15

SEQ ID NO: 22          moltype = DNA  length = 35
FEATURE                Location/Qualifiers
source                 1..35
                       mol_type = other DNA
                       organism = synthetic construct
SEQUENCE: 22
ctcgagacag ttcttcaact ggcagcttgc ggccg                      35

SEQ ID NO: 23          moltype = DNA  length = 29
FEATURE                Location/Qualifiers
source                 1..29
                       mol_type = other DNA
                       organism = synthetic construct
SEQUENCE: 23
ggccgcaagc tgccagttga agaactgtc                             29

SEQ ID NO: 24          moltype = DNA  length = 24
FEATURE                Location/Qualifiers
source                 1..24
                       mol_type = other DNA
                       organism = synthetic construct
SEQUENCE: 24
ctattgtcga gggagctaag aagt                                  24

SEQ ID NO: 25          moltype = DNA  length = 24
FEATURE                Location/Qualifiers
source                 1..24
                       mol_type = other DNA
                       organism = synthetic construct
SEQUENCE: 25
cgcaagctgc cagttgaaga actg                                  24

SEQ ID NO: 26          moltype = DNA  length = 24
FEATURE                Location/Qualifiers
source                 1..24
                       mol_type = other DNA
                       organism = synthetic construct
SEQUENCE: 26
ctattgtcga gggagctaag aagt                                  24

SEQ ID NO: 27          moltype = DNA  length = 21
FEATURE                Location/Qualifiers
source                 1..21
                       mol_type = other DNA
                       organism = synthetic construct
SEQUENCE: 27
gcgtcagaca aaccctaacc a                                     21
```